(12) United States Patent
Madrid et al.

(10) Patent No.: US 12,387,822 B2
(45) Date of Patent: Aug. 12, 2025

(54) MASS SPECTROMETRY DISTINGUISHABLE SYNTHETIC COMPOUNDS, LIBRARIES, AND METHODS THEREOF

(71) Applicant: SRI International, Menlo Park, CA (US)

(72) Inventors: Peter Madrid, Sunnyvale, CA (US); Nathan Collins, San Mateo, CA (US); Michal Avital-Shmilovici, Sunnyvale, CA (US); Pauline Bourbon, San Francisco, CA (US); Thomas Shaler, Fremont, CA (US)

(73) Assignee: SRI International, Menlo Park, CA (US)

( * ) Notice: Subject to any disclaimer, the term of this patent is extended or adjusted under 35 U.S.C. 154(b) by 630 days.

(21) Appl. No.: 16/644,565

(22) PCT Filed: Sep. 5, 2017

(86) PCT No.: PCT/US2017/050119
§ 371 (c)(1),
(2) Date: Mar. 5, 2020

(87) PCT Pub. No.: WO2019/050504
PCT Pub. Date: Mar. 14, 2019

(65) Prior Publication Data
US 2021/0065848 A1    Mar. 4, 2021

(51) Int. Cl.
*G16C 20/20* (2019.01)
*G16B 35/10* (2019.01)
*G16C 20/62* (2019.01)
*G16C 20/64* (2019.01)

(52) U.S. Cl.
CPC ............ *G16C 20/20* (2019.02); *G16B 35/10* (2019.02); *G16C 20/62* (2019.02); *G16C 20/64* (2019.02)

(58) Field of Classification Search
CPC ........ G16C 20/20; G16C 20/62; G16C 20/64; G16B 35/10
See application file for complete search history.

(56) References Cited

U.S. PATENT DOCUMENTS

| | | | |
|---|---|---|---|
| 5,186,898 A * | 2/1993 | Bridgham | C07K 1/045 220/636 |
| 5,792,431 A * | 8/1998 | Moore | B01J 19/0046 506/40 |
| 2002/0191825 A1 | 12/2002 | Parekh et al. | |
| 2003/0036854 A1* | 2/2003 | Desjarlais | G16B 35/00 702/19 |
| 2006/0194258 A1* | 8/2006 | Pirrung | G01N 21/6452 435/7.1 |
| 2007/0117099 A1* | 5/2007 | Engelhardt | C40B 60/14 435/6.12 |
| 2008/0167194 A1 | 7/2008 | Dahiyat et al. | |
| 2013/0053258 A1 | 2/2013 | Markiewicz et al. | |
| 2014/0323330 A1 | 10/2014 | Bergo | |
| 2015/0148242 A1 | 5/2015 | Magarvey et al. | |
| 2015/0217254 A1* | 8/2015 | Boroomand | B01J 19/0046 422/106 |

FOREIGN PATENT DOCUMENTS

| | | |
|---|---|---|
| EP | 1842433 A2 | 12/2004 |
| JP | 2002514811 A | 5/2002 |
| JP | 2004174331 A | 6/2004 |
| JP | 2008031105 A | 2/2008 |
| JP | 2011510300 A | 10/2012 |
| JP | 2013047624 A | 3/2013 |
| JP | 2013190422 A | 9/2013 |

OTHER PUBLICATIONS

Drewry, D. H.; Young, S. S. Approaches to the Design of Combinatorial Libraries. Chemometrics and Intelligent Laboratory Systems 1999, 48 (1), 1-20.*
Geysen, H. M.; Wagner, C. D.; Bodnar, W. M.; Markworth, C. J.; Parke, G. J.; Schoenen, F. J.; Wagner, D. S.; Kinder, D. S. Isotope or Mass Encoding of Combinatorial Libraries. Chemistry & Biology 1996, 3 (8), 679-688.*
Hoffmann, C.; Blechschmidt, D.; Krüger, R.; Karas, M.; Griesinger, C. Mass Spectrometric Sequencing of Individual Peptides from Combinatorial Libraries via Specific Generation of Chain-Terminated Sequences. Journal of Combinatorial Chemistry 2002, 4 (1), 79-86.*
Hughes, I. Design of Self-Coded Combinatorial Libraries to Facilitate Direct Analysis of Ligands by Mass Spectrometry. Journal of Medicinal Chemistry 1998, 41 (20), 3804-3811.*
Hurtado, P. P.; O'Connor, P. B. Differentiation of Isomeric Amino Acid Residues in Proteins and Peptides Using Mass Spectrometry. Mass Spectrometry Reviews 2012, 31 (6), 609-625.*
Krämer, T.; Antonenko, V. V.; Mortezaei, R.; Kulikov N. V. Encoding Technologies. Chapter 5 of Handbook of Combinatorial Chemistry: Drugs, Catalysts, Materials; Nicolaou, K. C., Hanko, R., Hartwig, W., Eds.; Wiley-VCH: Weinheim, 2002.*

(Continued)

*Primary Examiner* — Olivia M. Wise
*Assistant Examiner* — Dawn Bickham
(74) *Attorney, Agent, or Firm* — Dicke, Billig & Czaja, PLLC

(57) ABSTRACT

Embodiments in accordance with the present disclosure are directed to polymer beads and uses thereof, including forming libraries of compounds for screening and assay purposes. An example method includes using logic circuitry to: select a plurality of molecules that include a plurality of subgroups, each of the plurality of molecules exhibiting a mass spectrometry characteristic that is distinguishable from mass spectrometry characteristics of other molecules of the plurality, and assign the plurality of molecules with a position in a sequence of a plurality of synthetic compounds forming a library. The method further includes defining, as data in a memory circuit of the logic circuitry, the plurality of synthetic compounds that are sequenceable via mass spectrometry using the assigned positions of the plurality of molecules for communicating to other circuitry for formation thereof via coupling chemistry or screening of a particular function.

12 Claims, 30 Drawing Sheets

(56) References Cited

OTHER PUBLICATIONS

Shin, Y. G.; van Breemen, R. B. Analysis and Screening of Combinatorial Libraries Using Mass Spectrometry. Biopharmaceutics & Drug Disposition 2001, 22 (7-8), 353-372.*
Steinbeck, C.; Berlin, K .; Richert, C. MASP—A Program Predicting Mass Spectra of Combinatorial Libraries. Journal of Chemical Information and Computer Sciences 1997, 37 (3), 449-457.*
Wagner, D. S.; Markworth, C. J.; Wagner, C. D.; Schoenen, F. J.; Rewerts, C. E.; Kay, B. K.; Geysen, H. M. Ratio Encoding Combinatorial Libraries with Stable Isotopes and Their Utility in Pharmaceutical Research. Combinatorial Chemistry & High Throughput Screening 1998, 1 (3), 143-153.*
Blom, K. F. Strategies and Data Precision Requirements for the Mass Spectrometric Determination of Structures from Combinatorial Mixtures. Analytical Chemistry 1997, 69 (21), 4354-4362.*
Marx, H.; Lemeer, S.; Schliep, J. E.; Matheron, L.; Mohammed, S.; Cox, J.; Mann, M.; Heck, A. J. R.; Kuster, B. A Large Synthetic Peptide and Phosphopeptide Reference Library for Mass Spectrometry-Based Proteomics. Nature Biotechnology 2013, 31 (6), 557-564.*
Bryson, J. W.; Betz, S. F.; Lu, H. S.; Suich, D. J.; Zhou, H. X.; O'Neil, K. T.; DeGrado, W. F. Protein Design: A Hierarchic Approach. Science 1995, 270 (5238), 935-941.*
Hecht, M. H.; Das, A.; Go, A.; Bradley, L. H.; Wei, Y. De Novo Proteins from Designed Combinatorial Libraries. Protein Science 2004, 13 (7), 1711-1723.*
Kamtekar, S.; Schiffer, J. M.; Xiong, H.; Babik, J. M.; Hecht, M. H. Protein Design by Binary Patterning of Polar and Nonpolar Amino Acids. Science 1993, 262 (5140), 1680-1685.*

Extended European Search report for related European Patent Application No. 17924622.8 mailed on Mar. 9, 2021.
Lutz Weber: "Evolutionary combinatorial chemistry: application of genetic algorithms", Drug Discovery Today, vol. 3, No. 8, Aug. 1, 1998 (Aug. 1, 1998), pp. 379-385, XP055324927, Amsterdam, NL ISSN: 1359-6446, DOI: 10.1016/S1359-6446(98)01219-7.
Drewry D H et al: "Approaches to the design of combinatorial libraries", Chemometrics and Intelligent Laboratory Systems, Elsevier Science Publishers B.V. Amsterdam, NL, vol. 48, No. 1, Jun. 14, 1999 (Jun. 14, 1999), pp. 1-20, XP004167956, ISSN: 0169-7439, DOI: 10.1016/S0169-7439(99)00010-6.
Shin Y G et al.: "Analysis and screening of combinatorial libraries using mass spectrometry", Biopharmaceutics and Drug Disposition, Wiley, Chichester, US, vol. 22, No. 7-8, Oct. 1, 2001 (Oct. 1, 2001), pp. 353-372, XP002364332, ISSN: 0142-2782, DOI: 10.1002/BDD.278.
Hughes I: "Design of self-coded combinatorial libraries to facilitate direct analysis of ligands by mass spectrometry", Journal of Medicinal Chemistry, American Chemical Society, US, vol. 41, Aug. 29, 1998 (Aug. 29, 1998), pp. 3804-3811, XP002117710, ISSN: 0022-2623, DOI: 10.1021/JM9800954.
Nazarpack-Kandlousy N et al: "Regiochemical Tagging: A New Tool for Structural Characterization of Isomeric Components in Combinatorial Mixtures", Journal of the American Chemical Society, vol. 122, No. 14, Jan. 1, 2000 (Jan. 1, 2000), pp. 3358-3366, XP002501276,DOI: 10.1021/JA993844V [retrieved on Mar. 24, 2000].
Notification of Reasons for Refusal for related Japanese Patent Application No. 2020-513559 mailed on Jul. 6, 2021.
International Search Report and Written Opinion for related parent PCT Patent Application No. PCT/US2017/050119 mailed on Mar. 14, 2019.

* cited by examiner

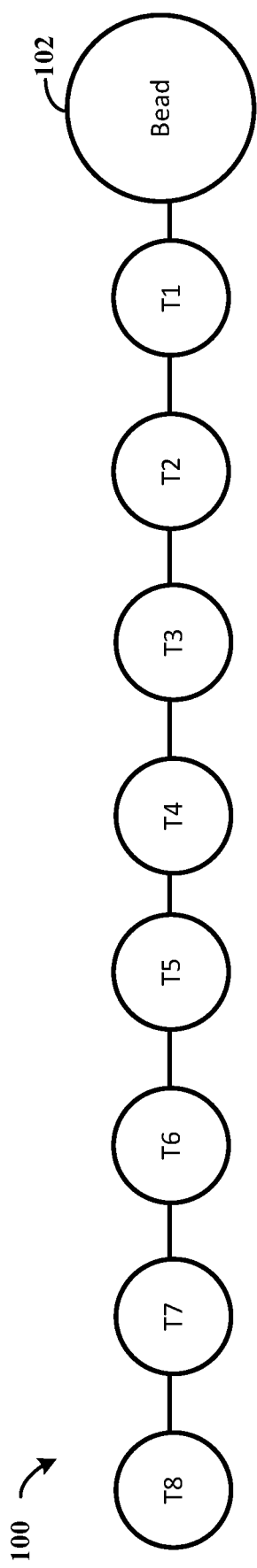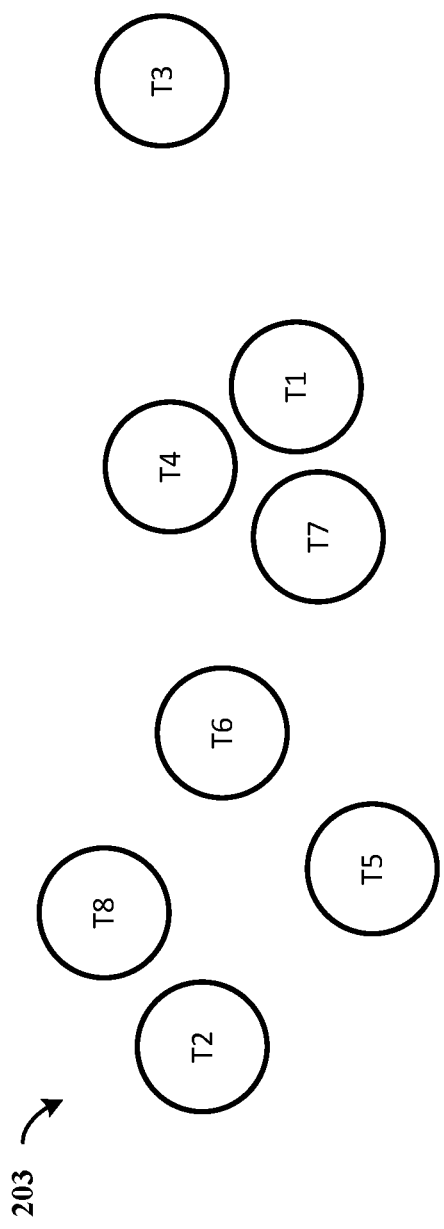
FIG. 1
FIG. 2

414
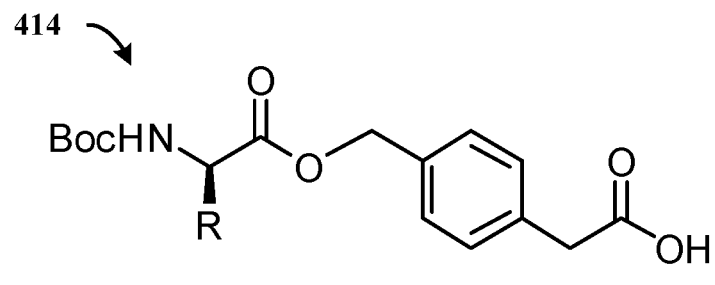
R = 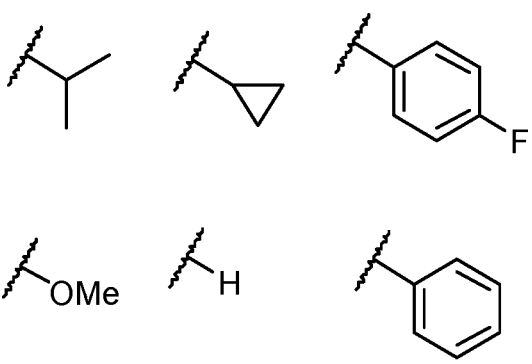
FIG. 4

Tetraptych 1:
1. Gly-DhqY-Ala-PAM
2. Gly-DhqB-Gly-PAM
3. Lys-DhqE-Phe-PAM
4. Ala-DhqE-Ala(Cp)-PAM
5. DhqY-Lys-Val-PAM
6. DhqY-Lys-Ser(Me)-PAM
7. DhqE-Gly-Phe(4F)-PAM
8. DhqY-Gly-Ala(Cp)-PAM

Tetraptych 2:
1. Ala-DhqO-Ala-PAM
2. Ala-DhqO-Gly-PAM
3. Lys-DhqF-Phe-PAM
4. Glu-DhqY-Ala(Cp)-PAM
5. DhqF-Lys-Val-PAM
6. DhqE-Gly-Ser(Me)-PAM
7. DhqO-Lys-Phe(4F)-PAM
8. DhqY-*Glu*-Phe-PAM

Tetraptych 3:
1. Glu-DhqB-Ala-PAM
2. Glu-DhqF-Gly-PAM
3. Gly-DhqB-Phe-PAM
4. Ala-DhqO-Ala(Cp)-PAM
5. DhqE-*Gly*-Val-PAM
6. DhqB-*Ala*-Ser(Me)-PAM
7. DhqF-*Ala*-Phe(4F)-PAM
8. DhqE-*Ala*-Gly-PAM

Tetraptych 4:
1. Lys-DhqF-Ala-PAM
2. Lys-DhqE-Gly-PAM
3. Glu-DhqF-Phe-PAM
4. Gly-DhqB-Ala(Cp)-PAM
5. DhqO-*Glu*-Val-PAM
6. DhqY-*Glu*-Ser(Me)-PAM
7. DhqB-*Glu*-Phe(4F)-PAM
8. DhqE-*Lys*-Ala-PAM

Tetraptych 5:
1. DhqB-*Gly*-Ala-PAM
2. DhqB-*Glu*-Gly-PAM
3. DhqF-*Ala*-Phe-PAM
4. DhqF-*Glu*-Ala(Cp)-PAM
5. Lys-DhqE-Val-PAM
6. Ala-DhqY-Ser(Me)-PAM
7. Ala-DhqE-Phe(4F)-PAM
8. Lys-DhqF-Phe(4F)-PAM

Tetraptych 6:
1. DhqE-*Glu*-Ala-PAM
2. DhqF-*Lys*-Gly-PAM
3. DhqE-*Gly*-Phe-PAM
4. DhqE-*Lys*-Ala(Cp)-PAM
5. Ala-DhqF-Val-PAM
6. Lys-DhqE-Ser(Me)-PAM
7. Gly-DhqY-Phe(4F)-PAM
8. Glu-DhqB-Val-PAM

Tetraptych 7:
1. DhqF-*Ala*-Ala-PAM
2. DhqY-*Gly*-Gly-PAM
3. DhqO-*Lys*-Phe-PAM
4. DhqB-*Ala*-Ala(Cp)-PAM
5. Gly-DhqO-Val-PAM
6. Gly-DhqF-Ser(Me)-PAM
7. Glu-DhqO-Phe(4F)-PAM
8. Glu-DhqB-Ser(Me)-PAM

Tetraptych 8:
1. DhqB-*Ala*-Ala-PAM
2. DhqE-*Lys*-Ala-PAM
3. DhqE-*Gly*-Ala-PAM
4. DhqO-*Lys*-Ala-PAM
5. Gly-DhqF-Ala-PAM
6. Glu-DhqE-Ala-PAM
7. Ala-DhqE-Ala-PAM
8. Glu-DhqB-Ala-PAM

FIG. 13A

| | | | | | | | |
|---|---|---|---|---|---|---|---|
| 1 | DhqB-*Ala*-Ala-PAM | DhqF-*Ala*-Ala-PAM | DhqE-*Glu*-Ala-PAM | DhqB-*Gly*-Ala-PAM | Lys-DhqF-Ala-PAM | Glu-DhqB-Ala-PAM | Ala-DhqO-Ala-PAM |
| 2 | DhqE-*Lys*-Ala-PAM | DhqY-*Gly*-Gly-PAM | DhqF-*Lys*-Gly-PAM | DhqB-*Glu*-Gly-PAM | Lys-DhqE-Gly-PAM | Glu-DhqF-Gly-PAM | Ala-DhqO-Gly-PAM |
| 3 | DhqE-*Gly*-Ala-PAM | DhqO-*Lys*-Phe-PAM | DhqE-*Gly*-Phe-PAM | DhqF-*Ala*-Phe-PAM | Glu-DhqE-Phe-PAM | Gly-DhqB-Phe-PAM | Lys-DhqF-Phe-PAM |
| 4 | DhqO-*Lys*-Ala-PAM | DhqB-*Ala*-Ala(Cp)-PAM | DhqE-*Lys*-Ala(Cp)-PAM | DhqF-*Glu*-Ala(Cp)-PAM | Gly-DhqB-Ala(Cp)-PAM | Ala-DhqO-Ala(Cp)-PAM | Glu-DhqY-Ala(Cp)-PAM |
| 5 | Gly-DhqF-Ala-PAM | Gly-DhqO-Val-PAM | Ala-DhqF-Val-PAM | Lys-DhqE-Val-PAM | DhqO-*Glu*-Val-PAM | DhqE-*Gly*-Val-PAM | DhqF-*Lys*-Val-PAM |
| 6 | Glu-DhqE-Ala-PAM | Gly-DhqF-Ser(Me)-PAM | Lys-DhqE-Ser(Me)-PAM | Ala-DhqY-Ser(Me)-PAM | DhqY-*Glu*-Ser(Me)-PAM | DhqB-*Ala*-Ser(Me)-PAM | DhqE-*Gly*-Ser(Me)-PAM |
| 7 | Ala-DhqE-Ala-PAM | Glu-DhqO-Phe(4F)-PAM | Gly-DhqY-Phe(4F)-PAM | Ala-DhqE-Phe(4F)-PAM | DhqB-*Glu*-Phe(4F)-PAM | DhqF-*Ala*-Phe(4F)-PAM | DhqO-*Lys*-Phe(4F)-PAM |
| 8 | Glu-DhqB-Ala-PAM | Glu-DhqB-Ser(Me)-PAM | Glu-DhqB-Val-PAM | Lys-DhqF-Phe(4F)-PAM | DhqE-*Lys*-Ala-PAM | DhqE-*Ala*-Gly-PAM | DhqY-*Glu*-Phe-PAM |

FIG. 13B

MASS SPECTROMETRY DISTINGUISHABLE SYNTHETIC COMPOUNDS, LIBRARIES, AND METHODS THEREOF

FEDERALLY-SPONSORED RESEARCH AND DEVELOPMENT

This invention was made with the support of the Defense Advanced Research Projects Agency (DARPA) and SPAWAR Systems Center Pacific (SSC Pacific) under Contract No. N66001-14-C-4059. The U.S. Government has certain rights in this invention.

OVERVIEW

Polymer beads can be used to form libraries of compounds, such as naturally or synthetically produced oligomers or polymers (e.g., peptides, non-peptides and small molecules). In some instances, the concept of "one-bead one-compound" (OBOC) combinatorial libraries can be used to generate different compounds. The library can be used to screen for compounds that react to a target or provide a particular function. The OBOC library can include the use of a split synthesis approach, and ultimately each bead has one chemical entity. Using such an approach, libraries of compounds can be synthesized and screened for hits, such as a hit of compound for particular purposes (e.g., binding to a target). Structural determination of a screened compound can be performed by Edman chemistry, ladder sequencing, or isotope encoding. The structural determination techniques can have limitations, such as the coding can interfere with the binding assay.

SUMMARY OF THE INVENTION

The present invention is directed to overcoming the above-mentioned challenges and others related to forming and screening libraries of compounds for particular purposes. Specific aspects are directed to methods of forming libraries of synthetic compounds, each compound including a sequence of molecules. The molecules are formed of one or more molecular subgroups (e.g., monomers or functional groups) and have molecular weights that can be distinguished by mass spectrometry.

Various aspects of the present disclosure are directed to methods of forming a library of synthetic compounds, such as oligomers or polymers. The library can be formed using logic circuitry that select a plurality of molecules, sometimes referred to as a "ptych", each formed of a plurality of subgroups and exhibiting different mass spectrometry characteristics. The library includes a plurality of synthetic compounds that include different sequential combinations of a plurality of molecules. Each of the synthetic compounds can be attached to a bead (e.g., a polymer bead). At least some of the molecules of the compound (e.g., molecules surrounded by other molecules and/or as attached to a bead) can include cleavable groups. The molecules, or ptychs, can be referred to with a prefix in front of ptych that denotes the number of subgroups in the molecule. For example, a molecule formed of four subgroups (e.g., four functional groups or monomers) can be referred to as a tetraptych and a molecule formed of three subgroups can be referred to as a triptych. The library is designed such that each molecule is associated with a different position or sequence order in the chain of the compounds of the library such that a mass spectrometry analysis of the molecules (e.g., read out of a particular molecular weight) identifies the position of the molecule in the compound as well as the composition or identity of the molecule, including the sequence of subgroups forming each molecule.

In various specific embodiments, logic circuitry is used to design the library. The plurality of molecules that include a plurality subgroups are selected by the logic circuitry. Each of the plurality of molecules can exhibit a mass spectrometry characteristic that is distinguishable from mass spectrometry characteristics of other molecules of the plurality. The logic circuitry can select the plurality of molecules from a set of potential molecules by identifying the plurality that have a mass spectrometry characteristic that are a threshold value from any other mass spectrometry characteristic of molecules in the plurality (e.g., the plurality is a subset of the set of potential molecules). The logic circuitry assigns the plurality of molecules with a position in a sequence of a plurality of synthetic compounds forming a library in a memory circuit of the logic circuitry. Further, the plurality of synthetic compounds that are sequenceable via mass spectrometry can be formed using the assigned positions of the plurality of molecules.

As a specific example, assume a library is being designed with compounds formed of eight molecules. Each compound in the library has eight positions for the molecules, with the first position being closest to the bead and the eighth position being furthest from the bead respectively. Each position is designed to have eight possible molecules in sequence, and can result in a total number of sixty-four (e.g., eight positions multiplied by eight possibilities at each position) distinguishable possible molecules that have different mass spectrometry characteristics. Example mass spectrometry characteristics include molecular weight, isotope distribution, elution time and fragmentation patterns identified from performing mass spectrometry. While the library can include $8^8$ different compounds, to identify a specific compound that is suspected of a desired function, only sixty-four different mass spectrometry characteristics (e.g., sixty-four weights molecular weights, sixty-four fragmentation patterns, sixty-four isotope distributions, sixty-four elution times and/or combinations thereof) are scanned for, which represent the sixty-four different molecules. As each molecule is also associated with a specific position, identification of the mass spectrometry characteristics (e.g., molecular weights, fragmentation patterns, elution times and/or isotope distributions) identifies the full composition of the compound. For example, the mass spectrometry characteristic of each molecule maps to the identity of the molecule, the position of the molecule in the compound, and the sequence of the subgroups included in the molecule. In this manner, the mass spectrometry characteristics of the molecules act as barcodes that identify the composition of the synthetic compound, e.g., the sequence of molecules that the synthetic compound is composed of. As the mass spectrometry characteristics are used to identify the composition of the synthetic compound, the detection sensitivities used to sequence the compounds are a function of or limited by the capabilities of mass spectrometry technology, which can currently limit the detection to one femtomole (fmol). In a number of aspects, various types of mass spectrometry inlet systems can be used such as directly coupling to an upfront chromatographic separation system such as a high performance liquid chromatography (HPLC) system.

In related aspects, the library is formed by designing a plurality of different molecules that exhibit distinguishable molecular weights. The different molecules include subgroups (e.g., functional groups or monomers) having distinguishable molecular weights, and the molecular weights of the molecules can be computed. Molecules having molecular weights that are distinguishable from one another via mass spectrometry, such as separable by five parts-per-million (ppm), are selected and used to form different compounds. The selected molecules are used to form a plurality of different compounds with each compound formed by the same number of molecules. As a specific example, a plurality of compounds are formed via a sequence of eight molecules. However, embodiments are not so limited, and the compounds can be polymers and/or oligomers and can be between 2-40 or more molecules long. Between at least some of the molecules includes a cleavage site that can be used to chemically separate, from one another, each of the molecules that form a compound. The cleavage sites are sometimes herein referred to as "cleavage groups". The compounds are (physically) formed using coupling chemistry to couple different molecules and/or subgroups. Each of the plurality of molecules is associated a position in a sequence order of compounds in the library based on the design of the compounds in the library. The positions can be stored in a memory circuit using logic circuitry. For example, when a particular molecule is present within a compound, it is known based on the library design that the particular molecule is always located at the assigned and/or correlated position. Each position can have a set of possible molecules that are assigned to the position. Using the above provided example, a library is designed that includes compounds formed by eight molecules in eight positions and each of the eight positions has a set of eight possible molecules. The library is used to screen for binding to a target and selected compounds that bind to the target are identified, isolated or plated using circuitry, and cleaved to separate the compound from the bead and/or to separate each molecule. In specific aspects, the selected compounds are isolated and/or plated using manual and/or automated methods of handling and separating beads. The cleavage can result in a mixture of the molecules, separated from one another, in solution. The mixture can be used to identify the sequence of the selected compound (e.g., the order of the molecules in the compound and the order of subgroups forming each molecule) by performing mass spectrometry and using the resulting mass spectrometry characteristics to identify both the molecules in the compound and the position of each molecule in the sequence of the compound. The compound, as selected and/or identified from the screening and mass spectrometry processes, and/or a conjugate form of the compound can be formed (using coupling chemistry) and used to provide a particular functionality, as further described below.

In other related and specific aspects, the molecules are designed by selecting a plurality of subgroups that exhibit mass spectrometry characteristics that are distinguishable from other subgroups in the plurality and correlating each of the plurality of subgroups with a position in a sequence of prospective molecules. The prospective molecules are then used to select the plurality of molecules which exhibit mass spectrometry characteristics that are separable (e.g., different) from other mass spectrometry characteristics by a threshold amount. As used herein, the term "distinguishable mass spectrometry characteristics" is sometimes interchangeable with the term "unique mass spectrometry characteristics" and includes or refers to values that are identifiable and/or otherwise distinguishable from the values of another subgroup and/or molecule in the library. The process can thereby include two different assignments. The first assignment includes selecting a set of subgroups among the plurality for each position in the sequence of prospective molecules, which is then used to select a plurality of molecules that exhibit distinguishable mass spectrometry characteristics. The second assignment includes selecting a set of molecules among the plurality for each position in the sequence of prospective synthetic compounds. The selected set of subgroups and the selected set of molecules that are assigned to positions in the molecules and compounds, respectively, can be correlated in memory, as further described herein.

Related aspects of designing the library include using the logic circuitry to assign and/or correlate the plurality of molecules with a position in a sequence of a plurality of synthetic compounds forming the (digital) library in a memory circuit of the logic circuitry and define the plurality of synthetic compounds that are sequenceable via mass spectrometry in the memory circuit using the assigned positions of the plurality of molecules. The defined library can be communicated to other circuitry for formation thereof via coupling chemistry or screening of a particular function. The logic circuit can communicate, as one or more data objects, the defined plurality of synthetic compounds and correlation of the molecules with the assigned position in the sequence to the other circuitry for formation of the library and/or screening for the function. The other circuitry or logic circuitry can be used to form, via coupling chemistry, the plurality of synthetic compounds based on the definition in the memory circuit, and/or to screen the plurality of synthetic compounds for a particular function.

Specific embodiments are directed to a library of a plurality of synthetic compounds. Each compound is formed of a plurality of molecules having mass spectrometry characteristics (e.g., molecular weights and/or resulting fragmentation patterns, elution times and/or isotope distributions) that identify the molecule and the position of the molecule in the sequence of the compounds. As previously described, the molecules are formed of different subgroups and are used to screen for binding to a target. Each of the plurality of molecules have a unique molecular weight and/or other mass spectrometry characteristic, and are associated with a position in the sequence (e.g., order) of compounds. For example, a first molecule has a first mass spectrometry characteristic and can only be in the first position of the compounds (e.g., closest to the bead) in the library. Upon performing mass spectrometry on a solution containing a mixture of molecules of a compound, if the first mass spectrometry characteristic (e.g., value of a molecular weight, associated fragmentation pattern, elution time and/or isotope distribution) is read as an output, the compound is known to have the first molecule in the first position. The library contains molecules having as many manmade functional groups, herein referred to as "subgroups", as possible and the mass spectrometry characteristics are used like barcodes to identify the composition of the compound (e.g., the sequence or order of molecules formed of respective functional groups). Using the above-described first molecule, the sequence order of the subgroups forming the first molecule is also known based on the design of the library, as previously described.

In various related aspects, the molecules used to form the library are patterned prior to forming the (physical) library of compounds and the pattern is used as reference pattern for error control. For example, mass spectrometry can be performed on each of the molecules to form a reference for comparison for later screening of the library. The results can provide a reference of the molecular weight, the fragmentation pattern, elution time and/or the isotope distribution (and/or chromatographic retention time). In implementations where mass spectrometry is combined with chromatographic separation such as HPLC, chromatographic retention time is an additional factor that can be used for confirmation. These references can be used to ensure results are not background noise. Subsequent screening can be performed and the composition of the compound can be identified via molecular weight, fragmentation pattern, elution time and/or isotope distribution. In further specific aspects, two or more molecules and/or subgroups may have molecular weights that are not distinguishable by molecular weight (e.g., are the same or within a threshold amount) but that are distinguishable by a second mass spectrometry characteristics, such as fragmentation pattern, elution time and/or isotope distribution.

As may be appreciated, the library formed can be data (e.g., a data object) stored in a memory circuit and/or can be formed physical chemical compounds. For example, the library can be designed using logic circuitry and can be stored as data in a memory circuit of and/or in communication with the logic circuitry. The compounds can be stored as data that identifies the sequence of molecules and the subgroups forming the molecules, and that additionally maps to identification of mass spectrometry characteristics of the molecules. The logic circuitry can communicate the library to equipment and/or other circuitry used to form the physical chemical compounds using coupling chemistry and/or circuitry for screening of the library for a particular function. In other aspects, the library includes a physical library of formed chemical structures (and is not stored in data but rather physical chemical structures that are formed or are additionally stored as data).

The method of designing the library and/or the designed library, as described above, can utilize fewer processing resources and/or memory resources of the logic circuitry than other design techniques or designed libraries as the correlated mass spectrometry characteristics and the resulting amount of data stored, which can be used to identify the sequence of the compounds, is a function of (or magnitude of) the number of molecules used rather than the number of compounds designed and/or the full sequence of the compounds including the subgroups. As the mass spectrometry characteristics map both to the identity of the molecule and the position of the molecule in the compound, the characteristics can be used to identify the full composition of the compound. For example, each molecule can map to the sequence of subgroups forming the molecule, such as a map stored in a memory circuit. As also previously described, the logic circuitry can communicate the data that maps the mass spectrometry characteristics to molecules and the positions in the sequence of compounds to circuitry used to analyze results from an assay. The circuitry, which in some aspects includes the same logic circuitry or another logic circuitry in communication with mass spectrometry circuitry, can compare mass spectrometry results to the map that correlates the mass spectrometry characteristics to molecules, positions in the sequence, and the subgroup sequence of the molecules. Similarly to the logic circuitry, the processing resources used by the circuitry analyzing the results can be reduced as compared other techniques described above as the circuitry searches and/or compares the known mass spectrometry characteristics of the plurality of possible molecules to the mass spectrometry results. As a specific example, while the library can include $10^{10}$ different compounds, to identify a specific compound that is suspected of a desired function, one hundred different mass spectrometry characteristics (e.g., one hundred molecular weights, one hundred fragmentation patterns, one hundred isotope distributions, and/or various combinations thereof) are scanned for and which represent the one hundred different molecules as each molecule is also associated with a specific position.

Specific embodiments are directed to a method of screening a library of sequenceable synthetic compounds formed of molecules having unique molecular weights and/or other mass spectrometry characteristics. The library includes a plurality of polymer beads, each bead having a different compound attached thereto. The library can be used to screen for reaction or interaction of the screening compound to a target, generate a diagnostic assay, and/or identification of new synthetic compounds that provide specific functionality. For example, an assay can be generated using the library of synthetic compounds and a target. The assay is screened for a synthetic compound of the plurality that exhibits a particular function, which is isolated. For example, respective compounds that are hits (e.g., react to the target), are identified by cleaving the compound into the separate molecules as a mixture in solution, and performing mass spectrometry on the resulting solution. As previously described, each compound in the library is formed of a unique sequence of a subset of a plurality of molecules. Each of the plurality of molecules have a mass spectrometry characteristic that can be identified using mass spectrometry. The respective masses (or resulting fragmentation pattern, elution time and/or isotope distribution) can map to, for example, via a map, key, or other association, a respective molecule and a position in the compound sequence, as well as a sequence of subgroups forming the molecule. The reacted bead can be used to identify the compound by separating the compound from the polymer bead, separating each of the molecules forming the compound from another in solution, and sequencing the synthetic compound by identifying mass spectrometry characteristics of the molecules via mass spectrometry (e.g., performing mass spectrometry on the solution to identify the composition of the compound). The compound can be used to form a pharmaceutical product used to treat an organism, for diagnosis purposes, as a sensor, as an enzyme, as a material for a particular purpose or to provide a particular functionality, among other uses.

Various related aspects are directed to systems used for screening a library. The systems can include the above-described library of synthetic compounds formed of molecules having unique molecular weights, an optical scanner, circuitry (e.g., selection circuitry) to find fluorescent hits and plate the respective compound. An example of an optical scanner is a fiber optic scanner, which includes a fiber optic bundle array, a laser, and imaging circuitry (e.g., camera). An assay is performed with the polymer beads to identify compounds exhibiting a particular function. In a specific example, the assay can be used to bind to a protein, inhibit an enzyme, and/or neutralize or kill a cell, among other functions. The detected activity is assessed via an optical (e.g., fluorescent) readout of the assay using an optical scanner. Identified beads having compounds that are suspected of exhibiting the particular function or activity are identified based on the scan and removed from the screening plate and placed in wells or tubes using the selection circuitry. Removed beads are further processed to release the compound from the bead and separate the molecules used to form the compound via cleavage, as previously described. The molecules used to form the compounds in the library have different mass spectrometry characteristics that can be identified using mass spectrometry and which can be used to sequence the synthetic compound.

In various other more specific embodiments, synthetic encoding compounds are used as barcodes to identify screening compounds. The synthetic encoding compounds are formed of subsets of the plurality of molecules with distinguishable mass spectrometry characteristics, as described above, and are located on an interior of beads in the library. The screening compounds, which are also synthetic, are located on the exterior of the beads. Each of the mass spectrometry characteristics of the synthetic encoding compounds can map to the screening compound and are used to sequence a screening compound that exhibits a particular function.

The above-described aspects can be used form a library of greater than 10^8 screening compounds that can be screened via mass spectrometry to identify the composition of the particular compound. In specific aspects, the library formed can be used to screen a plate of five million or more beads. For example, the library can be used to screen solid-support resins down to beads ten microns in diameter and with molecular loading of less than one-hundred femtomoles (fmol). Further, the molecules of the compound can be analyzed using mass spectrometry with sensitivities of greater than one fmol. The present invention is exemplified in a number of implementations and applications, some of which are summarized below as examples. Such libraries can be 10^8 or 10^9 (e.g., millions, billions or greater) of compounds in size or greater and can be used to screen for a reaction or interaction to at least one target, to generate a diagnostic assay, or for other target purposes/functions (e.g., a particular physical function).

Embodiments in accordance with the present disclosure include all combinations of the recited particular embodiments. Further embodiments and the full scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. All publications, patents, and patent applications cited herein, including citations therein, are hereby incorporated by reference in their entirety for all purposes.

BRIEF DESCRIPTION OF THE DRAWINGS

Various example embodiments may be more completely understood in consideration of the following detailed description in connection with the accompanying drawings, in which:

FIG. 1 illustrates an example of a compound including a plurality of molecules, in accordance with various embodiments;

FIG. 2 illustrates an example of a plurality of cleaved molecules, in accordance with various embodiments;

FIG. 4 illustrates an example of a cleavable group, in accordance with various embodiments;

FIGS. 13A-13B illustrate an example of a set of compounds formed of eight molecules, in accordance with various embodiments;

Figure 3:
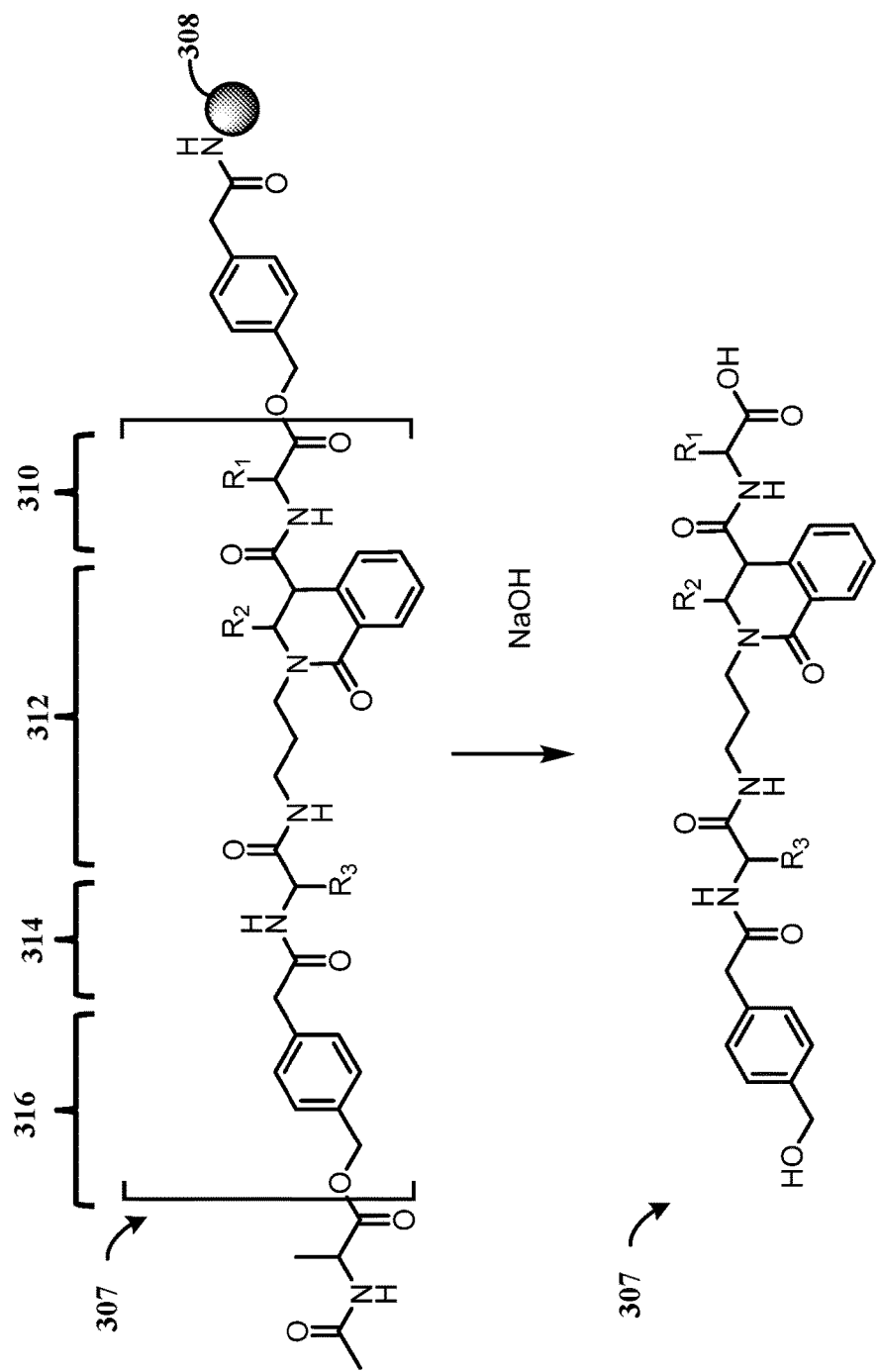
FIG. 3 illustrates an example molecule that includes a plurality of subgroups, in accordance with various embodiments.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION

Aspects of the present disclosure are believed to be applicable to a variety of synthetic compounds, methods of forming the same and methods for generating libraries of synthetic compounds that are distinguishable from one another via mass spectrometry. In certain implementations, each compound of the library can be sequenced via identification of mass spectrometry characteristics of molecules forming the compound. For example, the library is designed using a plurality of molecules formed of different functional groups, and each molecule has a distinguishable mass spectrometry characteristic as compared to other molecules of the plurality. The resulting compounds can subsequently be sequenced by performing mass spectrometry to identify which of the distinguishable mass spectrometry characteristics are present. While the present invention is not necessarily limited to such applications, various aspects of the invention may be appreciated through a discussion of various examples using this context.

Accordingly, in the following description various specific details are set forth to describe specific examples presented herein. It should be apparent to one skilled in the art, however, that one or more other examples and/or variations of these examples may be practiced without all the specific details given below. In other instances, well known features have not been described in detail so as not to obscure the description of the examples herein. For ease of illustration, the same reference numerals may be used in different diagrams to refer to the same elements or additional instances of the same element.

Various embodiments in accordance with the present disclosure are directed to a technique of designing and/or forming a library of synthetic compounds used for screening or other purposes. The library includes a plurality of polymer beads, each bead having a different compound attached thereto. More specifically, the library includes a plurality of synthetic compounds that include different sequential combinations of a plurality of molecules. The library can be used to screen for reaction or interaction of the compounds to a target, generate a diagnostic assay, and/or identification of new compounds that provide specific functionality. Each compound is formed of a plurality of different molecules that have known mass spectrometry characteristics and which are distinguishable (e.g., unique) relative to mass spectrometry characteristic of the other molecules in the plurality. Distinguishable or unique mass spectrometry characteristics, as used herein, includes or refers to a value of a mass spectrometry characteristic that is separable by a threshold from other values in the set of molecules and/or subgroups. Respective compounds that are hits (e.g., react to the target) are identified via mass spectrometry characteristics of the molecules that form the compound, such that the compounds can be used for diagnosis, treatment, or other purposes.

The mass spectrometry characteristics of the molecules of the compounds that are hits act as barcodes that are readout by performing mass spectrometry. For example, the molecules used to form the compounds in the library each have different (and known) molecular masses, fragmentation patterns, elution times and/or isotope distributions that can be identified using mass spectrometry. The respective mass spectrometry characteristics can map to, for example, via a map, key, or other association, a respective molecule and each molecule is assigned a position in the sequence of compounds formed in the library. As is further described herein, the molecules are formed of a plurality of subgroups, such as various functional groups. Each subgroup additionally has a distinguishable mass spectrometry characteristic and is assigned a position in the sequence of molecules of the library. The mass spectrometry characteristic thereby identifies the molecule itself, the position of the molecule in the sequence of the compound, as well as the sequence of subgroups forming the molecule.

The reacted bead can be used to identify the respective compound by separating the compound from the bead and the molecules from one another via cleavage and performing mass spectrometry. Mass spectrometry characteristics identified are compared to possible or known mass spectrometry characteristics of possible molecules in the library and are used to identify the sequence of the compound (e.g., the order of the plurality of molecules forming the compound which includes identification of the sequence of subgroups forming each molecule). Libraries formed in accordance with the present disclosure can be on an order of $10^8$ to $10^9$ or more compounds and can include beads that are sub-ninety microns in diameter, such as ten microns in diameter. The library can be screened using an optical scanner, as further described herein.

To form the above-described libraries, various embodiments include designing and screening a library of synthetic compounds on micron sized beads. The library can be screened to identify various functions, such as drugs, reagents, sensors or materials. The synthetic compounds, which can include polymers or oligomers, which are formed of a plurality of cleavable fragments, which are referred to herein as "molecules". The cleavable fragments have mass spectrometry characteristics that define the sequence of molecules forming the compound. The library can be formed by using logic circuitry to design molecules (e.g., the cleavable fragments) formed of different subgroups, analyzing the plurality of molecules to determine their mass spectrometry characteristics, selecting at least some of the molecules to use in the library based on their mass spectrometry characteristics, and assigning each of the selected molecules to a position in the sequence of compounds in the library. The molecules can be correlated with the assigned positions in a memory circuit of the logic circuitry. The library can be formed by synthesizing a plurality of compounds using the selected molecules and based on their assigned position and/or by defining each of the plurality of compounds as a data object stored in the memory circuit using the selected molecules and the assigned positions. The molecules can be selected to ensure that all of the mass spectrometry characteristics of the selected molecules are distinguishable from other selected molecules, such as their molecular weights being at least five parts-per-million (ppm) apart. Although embodiments are not so limited and can include different thresholds that separate the mass spectrometry characteristics. After selecting the molecules to use and assigning respective positions, the compounds can be synthesized using a combination of mix-and-split synthesis to synthesize the compounds on beads that are composed of multiple molecules with cleavable groups positioned between at least some of the multiple molecules. The cleavable groups can be inserted into the backbone of the compound and positioned between each molecule (e.g., ptych) at each mix-and-split step in the synthesis.

As may be appreciated, the library can be designed and stored as data in a memory circuit and/or can be physical chemical compounds. For example, the library can be designed using logic circuitry and can be stored as data (e.g., data object) in a memory circuit of and/or in communication with the logic circuitry. In other aspects, the library is designed and physically formed that includes a library of physically-formed chemical structures (and is not stored in data but rather a collections of physical chemical structures that are formed).

In various embodiments, the molecules are selecting by designing a set of prospective molecules and selecting the plurality of molecules from the set of prospective molecules. Each molecule is designed such that it can be cleaved into a single unit formed of a plurality of subgroups. A plurality of subgroups are selected that exhibit distinguishable mass spectrometry characteristics with respect to one another and each of the plurality of subgroups is assigned to a position in a sequence of the set of prospective molecules and/or the (assigned) position is correlated in memory. The plurality of molecules among the prospective molecules are selected that exhibit the distinguishable mass spectrometry characteristics, as previously described. In a number of embodiments, designing of the molecules and/or the compounds (e.g., selecting the subgroups, correlating subgroups with positions in the molecules to design different prospecting molecules, selecting the molecules, and correlating molecules with positions in the compounds) can occur using logic circuitry and can be stored in a memory circuit, as described above. Although embodiments are not so limited.

As a specific example, assume a library is being designed with compounds formed of ten molecules and each molecule is formed of three subgroups. Also assume that the library is designed with a total of thirty-five subgroups, with five possible subgroups at the first positon of the molecules and fifteen possible subgroups at the second and third positions of the molecules. Using the set of possible subgroups at each position in the molecule, a set of prospective molecules is designed that includes the subgroup sequences and the mass spectrometry characteristics of the molecules, which can be based on the sum of the mass spectrometry characteristics of subgroups forming the molecule. A plurality of the set of prospective molecules are selected that have distinguishable mass spectrometry characters for use in the library. As previously described, in such an example, each compound in the library has ten positions for the molecules, with the first position being closest to the bead and the tenth position being furthest from the bead respectively. Each position is designed to have ten possible molecules, resulting in a total number of one hundred (e.g., ten multiplied by ten) different molecules with unique molecular weights and/or other different mass spectrometry characteristics. Further, each compound includes a total of thirty subgroups (e.g., ten molecules multiplied by three subgroups per molecule). While the library can include $10^{10}$ different compounds, to identify a specific compound that is suspected of a desired function, only one hundred different mass spectrometry characteristics (e.g., one hundred molecular weights, one hundred fragmentation patterns, or one hundred isotope distributions and/or various combinations of molecular weights, fragmentation patterns, elution times and/or isotope distributions) are scanned for and which represent the one hundred different molecules as each molecule is also associated with a specific position. The mass spectrometry characteristics map both to the identity of the molecule and the position of the molecule in the compound, and can be used to identify the full composition of the compound. For example, each molecule can map to the sequence of subgroups forming the molecule, such as a map stored in a memory circuit. As the mass spectrometry characteristics are used to identify the composition of the synthetic compound, including both the sequence of molecules and the sequence of subgroups forming the molecules, the detection sensitivities are a function of or limited by the capabilities of mass spectrometry equipment and/or technology (e.g., a mass spectrometer), which can currently limit the detection to one fmol. Such detection sensitivities allow for use of beads that are smaller than ninety microns, such as ten micron beads, and for screening of a library that is 10^8 or 10^9 (e.g., millions or billions) of compounds in size.

In various related embodiments, the molecules used to form the library are patterned prior to forming the library and used as an error control. For example, mass spectrometry can be performed on each of the selected molecules to form a reference for comparison for later screening of the library. The results can provide a reference of the molecular weight, the fragmentation pattern, elution time, isotope distribution and/or chromatographic retention time when relevant to isotope distribution. These references can be used to ensure results are not background noise. In this manner, subsequent screening can be performed and the composition of the compound can be identified via molecular weight, fragmentation patterns isotope distributions, and/or chromatographic retention time, in some embodiments.

The library of synthetic compounds can be used to screen for new compounds having particular functions. The library can be used to screen for reaction or interaction of the screening compound to a target, generate a diagnostic assay used for screening purposes, and/or identification of new compounds that provide specific functionality. Respective screening compounds that are hits (e.g., react to the target), are identified by cleaving the compound into the separate molecules and performing mass spectrometry on the resulting solution. For example, each compound in the library is formed of a unique sequence of a subset of a plurality of molecules and each molecule is formed of a unique sequence of a subset of a plurality of subgroups. The respective masses (or resulting fragmentation pattern, elution time, isotope distribution and/or chromatographic retention time) can map to, for example, via a map, key, or other association, a respective molecule, a position of the molecule in the compound sequence, and a sequence of subgroups forming the molecule. The reacted bead can be used to identify the compound by separating the compound from the bead, separating each of the molecules forming the compound from another in solution, performing mass spectrometry on the solution, and identifying masses indicative of the subset of molecules and (which maps to) a respective position in the sequence of the compound and, also the sequence of subgroups forming the molecule.

In accordance with a number of specific embodiments, the above-described methods and/or polymer beads can be used to generate a library of 10^8 to 10^9 (or more) synthetic compounds. Each compound is attached to a single polymer bead. The library can be screened for hits to a target, such as using an optical scanner. An example of an optical scanner is a fiber optic scanner, which includes a fiber optic bundle array, a laser, and imaging circuitry (e.g., camera), such as Fiber-optic Array Scanning Technology (FAST). The FAST technology is based on the concept of "copying" a plate containing beads with a scanning laser and collecting a high resolution capture image of the plate using a densely packed fiber optic array bundle. The FAST system can allow for rapid scanning at speeds of between 1 million and 25 million cells per minute. For more specific and general information regarding an example FAST system, reference is made to Hsieh H B, Marrinucci D, Bethel K, et al., "High speed detection of circulating tumor cells", Biosensors and Bioelectronics, 2006; 21: 1893-1899, and Krivacic R T, Ladanyi A, Curry D N, et al., "A rare-cell detector for cancer", Proc Natl Acad Sci USA, 2004;101: 10501-10504, each of which are fully incorporated herein by reference.

An assay can be performed with the beads to identify compounds exhibiting a particular function. In specific examples, the assay can be used to bind to a protein, inhibit an enzyme, and neutralize or kill a cell, among other functions. The assay can be screened to identify a compound that exhibits a particular function and the identified compound can be isolated. For example, the detected activity is assessed via a fluorescent readout of the assay using an optical scanner. Identified beads that are suspected of exhibiting the particular function or activity are identified based on the scan and removed from the screening plate and placed in wells or tubes using the selection circuitry. Removed beads are further processed to release the compound on the bead and separate the molecules used to form the compound via cleavage, as previously described. The respective mass spectrometry characteristics of the molecules present map to, for example, via a map, key, or other association, the molecule and a position in the sequence of the compound, which is used to sequence the synthetic compound.

In various related embodiments, the synthetic compounds are used as barcodes to identify screening compounds. The synthetic compounds, sometimes herein referred to as "synthetic encoding compounds", are formed of subsets of the plurality of molecules with unique mass spectrometry characteristics and are located on an interior of beads in the library. The screening compounds, which are also synthetic, are located on the exterior of the beads. Each mass spectrometry characteristics of the synthetic encoding compounds can map to the screening compound and are used to sequence a screening compound that exhibits a particular function responsive to screening of the library.

As may be appreciated and as used herein, a polymer bead includes or refers to a polymer material formed in a three-dimensional shape, such as a sphere, an ellipsoid, oblate spheroid, and prolate spheroid shapes. Compound (sometimes referred to as a "screening compound") includes or refers to an oligomer or polymer formed in a library that is used to test for different functionalities, such as binding to a target, neutralizing or killing a target, and/or providing physical properties, among other functionalities. A library of synthetic compounds, as described above, includes or refers to a plurality of synthetic compounds, which can be designed and stored as data in a memory circuit and/or can be physical chemicals that are synthesized and used to screen for various functionality. In some specific embodiments, the physical chemicals are each connected to polymer bead.

Accordingly, in some specific embodiments, a library of synthetic compounds includes a plurality of different polymer beads, each bead coupled to a different physically-made synthetic compounds. Molecule, sometimes referred to as a "ptych", includes or refers to a set of subgroups bonded together. As described herein, the molecules are distinguishable from one another via mass spectrometry characteristics and can be formed of a plurality of subgroups. Subgroup includes or refers to a monomer or functional group. The plurality of subgroups can exhibit different functional characteristics. A functional group includes or refers to a group of atoms and/or bonds within a molecule (e.g., the polymer bead) that are responsible for a characteristic chemical reaction of the molecule. A cleavable group includes or refers to a functional group that cleaves to chemically separate molecules from one another and/or the compound from the bead. In various embodiments, the cleavable group is a subgroup of one or more of the plurality of molecules. Mass spectrometry characteristics includes or refers to properties or values observed from performing mass spectrometry on a compound, molecule, and/or mixture of molecules. Example mass spectrometry characteristics include molecular weighs, fragmentation patterns, elution times, isotope distributions, and chromatographic retention times (e.g., chromatographic retention isotope distribution). Encoding compound, sometimes also referred to as synthetic encoding compound, includes or refers to a peptide, oligomer, polymer, or other sequence of compounds or molecules which labels a respective screening compound. In various embodiments, the encoding compounds is the above-described compound designed using distinguishable molecules. Screening compound, sometimes also referred to as a synthetic screening compound, includes or refers to a compound used to screen for functionality of activity, such as binding to a protein. The screening compound, in various embodiments, includes the above-described compound designed using distinguishable molecules. In other embodiments, the screening compound is designed using other techniques. Topologically segregated includes or refers to a polymer bead with an interior surface and exterior surface having different molecules and/or compounds therein. Exterior surface of the polymer bead includes or refers to the outside of the polymer bead, which may come in contact with the surrounding environment and/or solution. Interior surface of the polymer bead includes or refers to the inside of the polymer bead. The interior surface can define the hollow cavity of a hollow bead, for example. Protecting group includes or refers to a compound and/or molecule that is introduced into another compound and/or molecule by chemical modification of a functional group (e.g., $NH_2$) to obtain chemoselectivity in a subsequent chemical reaction. Protected group includes or refers to a molecule or compound that is protected by the protecting group, which can include a functional group or form thereof and is sometimes herein interchangeably referred to as a "protected functional group". Deprotecting group includes or refers to a compound and/or molecule which is used to remove a protecting group. For example, a deprotecting group can be used to chemically modify a compound and/or molecule to remove the protecting group and/or to obtain the functional group (e.g., the deprotected group). A deprotected group is sometimes herein interchangeably referred to as a "deprotected functional group". A deprotected group or a deprotected functional group includes or refers to a resulting molecule or compound formed by reacting another molecule or compound having a protected group with a deprotecting group, which results in exposing the functional group. The protected group and deprotected group (e.g., functional groups that are protected or not protected) can each include different forms of an amine group, such as NH and $NH_2$. Assigning a subgroup to a position in molecules and/or assigning a molecule to a position in compounds includes or refers to identification or selection of a position that the respective subgroup or molecule is associated with. Correlating a subgroup to a position in molecules and/or correlating a molecule to a position in compounds in a memory circuit includes or refers to storing an association (e.g., data object, table, map) of the subgroup/molecule and the respective position in the memory circuit.

Turning now to the figures, FIG. 1 illustrates an example of a compound 100 including a plurality of molecules, in accordance with various embodiments. The compound 100 includes a synthetic polymer or oligomer that is formed of a plurality of molecules T1-T8 and is coupled to a polymer bead 102. The molecules T1-T8 are designed to be chemically diverse and sequenceable through the introduction of cleavable groups between at least some of the molecules T1-T8 along the chain of the compound. As further illustrated and described by FIG. 3, each molecule includes a plurality of subgroups, which provides the chemical diversity.

Various embodiments include forming a plurality of different compounds as a library. Such libraries can be 10^8 or 10^9 (e.g., millions or billions) of compounds in size and can be used to screen for a reaction or interaction to at least one target, to generate a diagnostic assay, or for other target purposes/functions. The library is designed using a computational design approach such that the compounds can be cleaved into fragments with distinguishable mass spectrometry characteristics. The plurality of synthetic compounds can include different sequential combinations of a plurality of molecules. In some embodiments, each compound in the library includes a plurality of molecules with cleavable groups positioned between at least some of the molecules that are formed using known mix-and-split synthesis techniques. The compounds are formed using a plurality of molecules, sometimes referred to as a "ptych", each having different mass spectrometry characteristics, such as molecular weighs, fragmentation patterns, elution times, and isotope distributions. In various embodiments, the molecules may also possess different chromatographic retention times. The library can be designed such that each molecule with a distinguishable mass spectrometry characteristic is associated with a different position or order in the sequence of the compounds of the library. In some examples, mass spectrometry analysis of the molecules (e.g., read out of a particular molecular weight) identifies the position of the molecule in the compound as well as the composition or identity of the molecule, including the sequence of subgroups forming the molecule.

FIG. 2 illustrates an example of a plurality of cleaved molecules T1-T8 of the compound 100 illustrated by FIG. 1, in accordance with various embodiments. The compounds of the library can be used to screen for different functions and to identify new compounds that can exhibit particular functions. As previously described, the compound is designed to have cleavable groups between at least some of the molecules. Compounds that exhibit the function can be sequenced via mass spectrometry by performing one or more cleavages to remove the compound from the bead and/or separate the plurality of molecules T1-T8 from one another and performing mass spectrometry on the solution. As a specific example, the isolated bead having the compound 100 attached thereto, illustrated by FIG. 1, is placed in contact with a solution that cleaves (or otherwise is cleaved) the compound resulting in a solution 203 of the molecules T1-T8, separated from one another, in solution. The cleavage can be performed via chemical, physical (e.g., temperate), light induced and/or biological/enzymatic methods, among other techniques. Example solutions can include NaOH and trifluoroacetic acid (TFA), among other cleavage solutions.

The solution 203 containing the mixture of the molecules T1-T8 can be analyzed to identify the composition of the compound. For example, mass spectrometry is performed on the solution 203 to identify the mass spectrometry characteristics present in the solution 203. Known mass spectrometry characteristics of the plurality of possible molecules can be searched for in each assigned position. In response to a match, the mass spectrometry characteristic identifies the molecule, as well as both the position of the molecule in the sequence order of the compound and the sequence order of subgroups forming the molecule.

Using the example illustrated by FIGS. 1 and 2, the compound 100 includes eight molecules in eight different positions (e.g., molecules T1-T8). Assume that the library of compounds includes a set of eight possible molecules at each of the eight positions. Responsive to performing mass spectrometry on the solution 203, sixty-four (e.g., eight possibilities molecules times eight positions) different mass spectrometry characteristics are compared to the mass spectrometry results to identify the composition of the compound 100. The library generated using such example numbers, on the other hand, can include $8^8$ different compounds. The mass spectrometry results, in the example illustrated by FIG. 2, results in identification of the molecules T1-T8 which each map to a specific position in a sequence of the compound and to the sequence of subgroups forming each respective molecule of T1-T8. The results can allow for identification of the sequence of the compound 100 illustrated by FIG. 1 from a solution 203 that includes a mixture of the plurality of molecules T1-T8 (and which are not necessarily in the correct order when obtaining the mass spectrometry results).

The mass spectrometry characteristics (e.g., molecular weights, fragmentation patterns, elution times and/or isotope distribution) thereby map both to the identity of the molecule and the position of the molecule in the compound, and can identify the full composition of the compound including the sequence of order of subgroups forming the compound. In this manner, the mass spectrometry characteristics of the molecules can act as barcodes that identifies the composition of the synthetic compound.

FIG. 3 illustrates an example molecule 307 that includes a plurality of subgroups 310, 312, 314, and 316, in accordance with various embodiments. As previously described, the library is formed by designing a plurality of different molecules with distinguishable mass spectrometry characteristics. The different molecules are formed of subgroups (e.g., functional groups or monomers). One or more of the subgroups can be designed to perform different functions or otherwise provide chemical diversity.

The molecules, or ptychs, can be referred to with a prefix in front of ptych that denotes the number of subgroups in the molecule. For example, a molecule formed of four subgroups (e.g., functional groups or monomers) can be referred to as a tetraptych and a molecule formed of three subgroups can be referred to as a triptych. As illustrated by the specific example of FIG. 3, the molecule 307 includes four subgroups 310, 312, 314, and 316 and is coupled to a polymer bead 308. Each or at least some of the subgroups 310, 312, 314, and 316 provide different functionalities. For example, the first subgroup 310 can include a group to indicate the position in the sequence, the second subgroup 312 can include a DHQ monomer, the third subgroup 314 can include an amino acid (D-amino acid), and the fourth subgroup 316 can include a cleavable group. Various functionality provided can include cleavage, binding to proteins, binding to other targets, etc. The cleavable group, in specific embodiments, can be a group that is cleaved in response to reaction with a solution. Another cleavable group can couple the molecule 307 to a polymer bead 308. Example cleavable groups can include Poly-acrylamide (PAM) that can cleave in response to being placed in contact with a solution containing NaOH.

FIG. 4 illustrates an example of a cleavable group 414, in accordance with various embodiments. As illustrated, the cleavable group 414 includes PAM which can cleave when placed in contact with a solution containing NaOH. Different types of PAMs can include different R-groups as illustrated by FIG. 4.

Figure 5A:
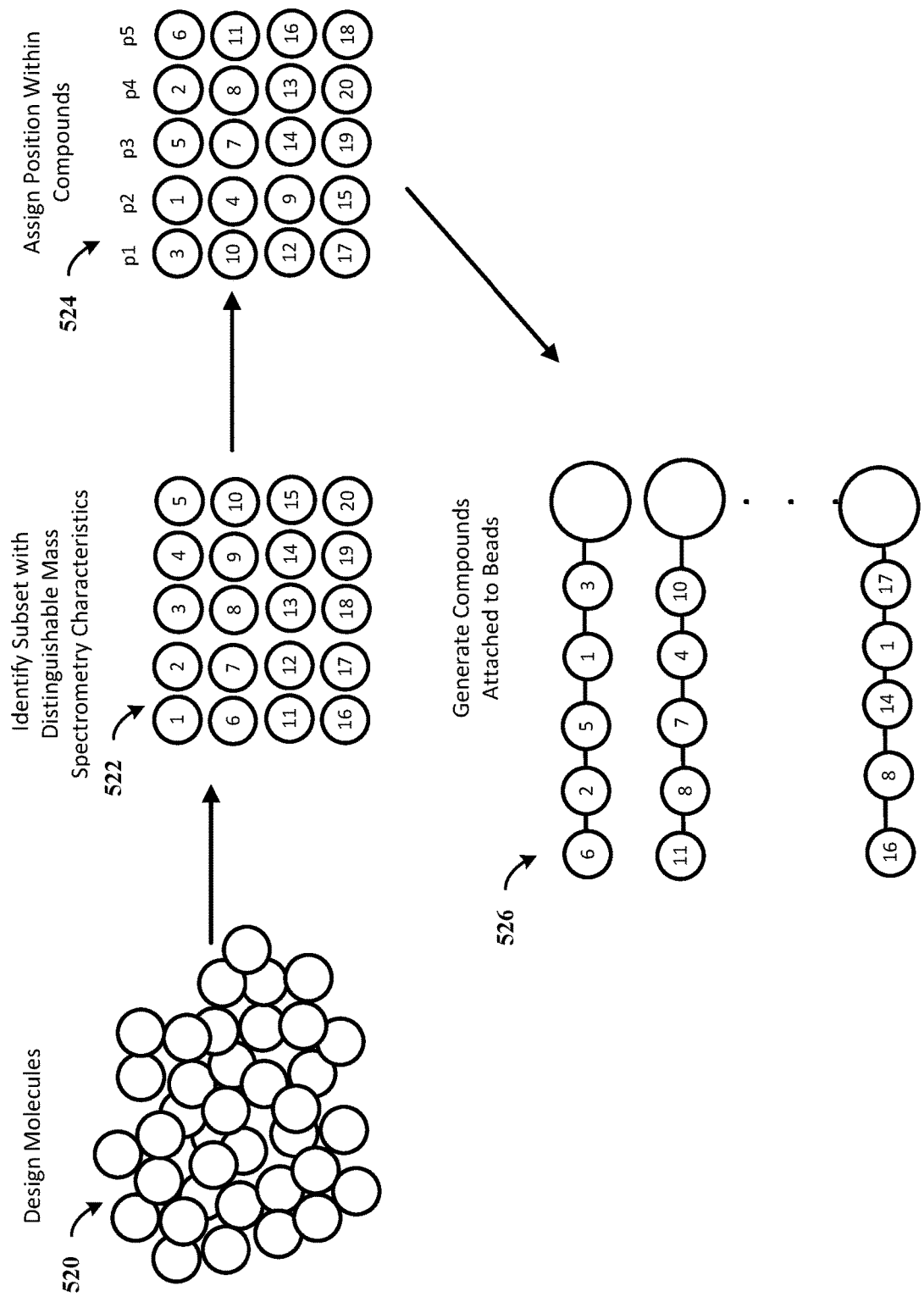
FIGS. 5A-5B illustrate example processes for forming a library of a plurality of compounds, in accordance with various embodiments.
Figure 5B:
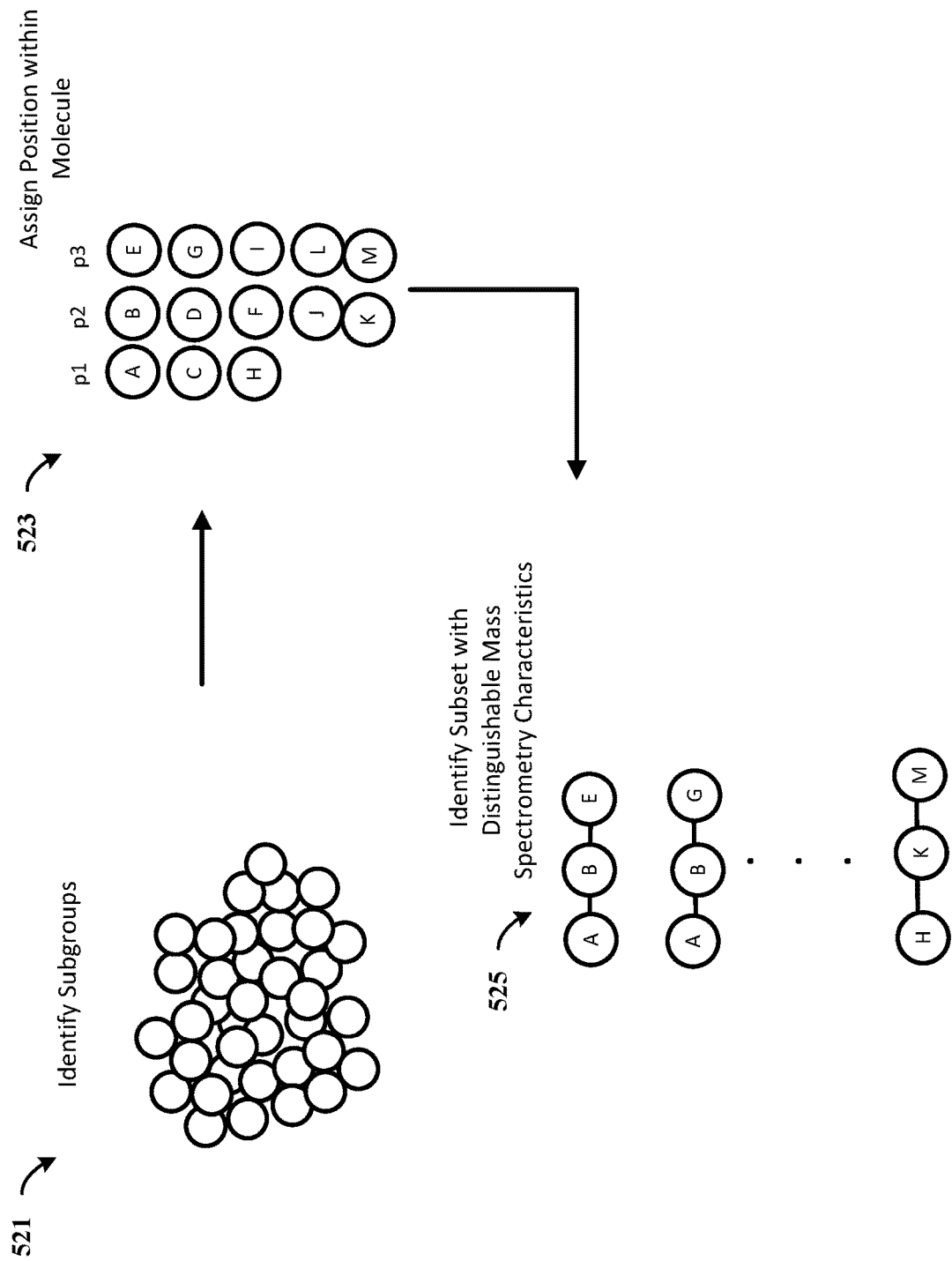

FIGS. 5A-5B illustrate example processes for forming a library of a plurality of compounds, in accordance with various embodiments. As illustrated by FIG. 5A, a plurality of different molecules are designed that include different subgroups groups, at 520. The plurality of different molecules can be designed to provide chemical diversity, as further illustrated and described in connection with FIG. 5B. At 522, a subset of the plurality of molecules are selected based on their molecular spectrometry characteristics. For example, the subset can be selected by computing the molecular weights of the plurality of molecules and selecting molecules with molecular weights that are distinguishable from one another. In some embodiments, the selected molecules have molecular weights that are at least five ppm separated from the molecular weights of the other selected molecules. Although embodiments are not limited and in some specific embodiments, mass spectrometry can be performed on the plurality of molecules and the subset is selected based on the fragmentations patterns or solutions times being distinguishable.

In various specific embodiments, mass spectrometry is performed on the subset of molecules and used as error control. For example, the mass spectrometry results in identification of the mass spectrometry characteristics of fragmentation patterns, elution times and isotope distributions, and which can be used to distinguish from background noise in subsequent mass spectrometry analysis.

The selected molecules are used to form a plurality of different compounds with each compound formed by the same number of molecules. Although embodiments are not so limited and the compounds can be formed of different numbers of molecules. The library is designed by selecting a number of molecules that are in sequence for each compound (e.g., how many molecules form each compound) and assigning respective molecules to a position in the sequence of prospective compounds, at 524. Each position can have a set of possible molecules that are assigned to the position. For example, the compounds are selected to have five molecules in sequence as illustrated by the example embodiment of FIG. 5A. The first position, which is closest to the bead, has a set of possible molecules of 3, 10, 12, and 17. The second position has a set of possible molecules of 1, 4, 9, and 15. The third position has a set of possible molecules of 5, 7, 14, and 19. The fourth position has a set of possible molecules of 2, 8, 13, and 20, and the fourth position has a sect of possible molecules of 6, 11, 16, and 18.

The molecules are then used to form a library of compounds by designing compounds using the set of possible molecules at each position. Using the example illustrated by FIG. 5A, the library can have $5^5$ different compounds. For example, at 526, the compounds are formed using coupling chemistry to couple different subgroups and/or molecules together. Between each molecule includes a cleavage group that can be used to separate each of the molecules in solution.

The selected molecules can be used to form a plurality of different compounds with each compound formed by the same number of molecules. For example, a plurality of compounds are formed via a sequence of five molecules. Although the embodiment of FIG. 5A illustrates a particular number of molecules used to form each compound, embodiments are not so limited and can include different number of molecules forming different compounds. Furthermore, embodiments are not limited to the number of molecules and/or the number of possible molecules in each position as illustrated. Various embodiments include libraries formed that are sized based on: (the number of possible molecules at each position)^(number of positions in the compounds). The compounds can be polymer or oligomers, in various embodiments, and can be between 2-40 or more molecules long.

FIG. 5B illustrates an example process for designing a plurality of different molecules that include different subgroups groups, such as previously illustrated at 520 of FIG. 5A. At 521, a plurality of different subgroups are identified. The plurality of different subgroups can have distinguishable mass spectrometry characteristics (e.g., masses) with respect to one another. In other embodiments, a set of the plurality is selected that has distinguishable mass spectrometry characteristics. At 523, each of the plurality of subgroups with distinguishable mass spectrometry characteristics is assigned to a position in the sequence of prospective molecules. As a specific example illustrated by FIG. 5B, there are three subgroups in each molecule with three possible subgroups at the first position (e.g., subgroup A, C, and H), five possible subgroups at the second position (e.g., subgroups B, D, F, J, and K), and five possible subgroups at the third position (e.g., subgroups E, G, I, L, and M). Each molecule, which can be referred to as a triptych, can be one of the prospective 75 choices (e.g., three times five times five).

At 525, a subset of the set of prospective molecules are selected that exhibit distinguishable mass spectrometry characteristics. For example, the mass spectrometry characteristic for molecule in the set of prospective molecules is determined by summing the mass spectrometry characteristics of the subgroups forming the respective molecules. A subset of the prospective molecules are selected that exhibit mass spectrometry characteristics that are different or separable from mass spectrometry characteristics of other molecules in the subset by a threshold value. For example, the difference of the nearest mass spectrometry value for each prospective molecule can be calculated and used to select the subset. As the mass spectrometry characteristics are used to identify the composition of the synthetic compound, including both the sequence of molecules and the sequence of subgroups forming the molecules, the detection sensitivities are a function of or limited by the capabilities of mass spectrometry technology, which can currently limit the detection to one fmol.

As a particular example, Table 1 illustrates an example design of a set of subgroups used to design molecules used to form the library of compounds:

TABLE 1

Subgroups and Assignment in Sequence of the Molecules

| Position 1 | | | Position 2 | | | Position 3 | | |
|---|---|---|---|---|---|---|---|---|
| 1. | Ala-COOH | 88.0399 | 1. | Ala | 71.0371 | 1. | Glycolic-Ala | 130.0504 |
| 2. | Phe-COOH | 164.0712 | 2. | Phe | 147.0684 | 2. | Glycolic-Phe | 206.0817 |
| 3. | Gly-COOH | 74.0242 | 3. | Gly | 57.0215 | 3. | Glycolic-Gly | 116.0348 |
| 4. | Leu-COOH | 130.0868 | 4. | Leu | 113.0841 | 4. | Glycolic-Leu | 172.0974 |
| 5. | Val-COOH | 116.0712 | 5. | Val | 99.0684 | 5. | Glycolic-Val | 158.0817 |
| | | | 6. | Glu | 129.0426 | 6. | Glycolic-Glu | 188.0559 |
| | | | 7. | His | 137.0589 | 7. | Glycolic-His | 196.0722 |
| | | | 8. | Lys | 128.095 | 8. | Glycolic-Lys | 187.1083 |
| | | | 9. | Asn | 114.0429 | 9. | Glycolic-Asn | 173.0562 |
| | | | 10. | Trp | 186.0793 | 10. | Glycolic-Trp | 245.0926 |
| | | | 11. | Arg | 156.1011 | 11. | Glycolic-Arg | 215.1144 |
| | | | 12. | Pro | 97.0528 | 12. | Glycolic-Pro | 156.0661 |

TABLE 1-continued

Subgroups and Assignment in Sequence of the Molecules

| Position 1 | | | Position 2 | | | Position 3 | |
|---|---|---|---|---|---|---|---|
| | 13. | Ser | 87.032 | 13. | Glycolic-Ser | 146.0453 |
| | 14. | Thr | 101.0477 | 14. | Glycolic-Thr | 160.061 |
| | 15. | Tyr | 163.0633 | 15. | Glycolic-Tyr | 222.0766 |

As illustrated, the subgroups are used to form molecules having three subgroups and each subgroup is assigned to a position in the prospective molecules (e.g., position 1, position 2, and position 3). The assigned positions of the subgroups can be correlated in a memory circuit of logic circuitry, such as by storing Table 1 in the memory circuit. Table 1 thereby identifies the set of subgroups used to form prospective molecules, their assigned position within the prospective molecules, and their mass spectrometry characteristics. Using the molecules, another table can be formed that includes the set of prospective molecules, resulting in a total of 1,125 prospective molecules (e.g., five x fifteen x fifteen) and their calculated mass spectrometry characteristics (e.g., a sum of the masses of the subgroups forming the respective molecules). Further, the mass spectrometry characteristics of the prospective molecules can be compared to identify a plurality of the prospective molecules having distinguishable mass spectrometry characteristics. In some specific embodiments, a determination of a ppm difference between the mass spectrometry characteristic of each molecule and the closest mass spectrometry characteristic of another prospective molecule can be made, and used to select molecules having mass spectrometry characteristics that are different or separable from one another by a threshold value (e.g., mass weights that are at least five ppm different than other mass weights).

The process of designing the library can include the use of logic circuitry to select a plurality of molecules that include a plurality of subgroups, correlate the plurality of molecules with a position in a sequence of a plurality of synthetic compounds in a memory circuit of the logic circuitry, and define (or form a data object including) the plurality of synthetic compounds that are sequenceable via mass spectrometry in the memory circuit using the correlated positions of the plurality of molecules for communicating to other circuitry for formation thereof via coupling chemistry or screening of a particular function. In some embodiments, the logic circuitry can be used for forming and/or screening the library, and/or the logic circuitry can communicate to other (external) circuitry for formation and/or screening of the library. For example, the logic circuitry can communicate one or more data objects that include the defined plurality of synthetic compounds and the correlation of the molecules with the position in the sequence to the other circuitry. A data object, as used herein, can include or refer to a data structure, function, variable or method used to store or reference data in a location, such as a table, index, and/or a location in memory having a value and referenced by an identifier. The other circuitry or logic circuitry can be used to form, via coupling chemistry, the plurality of synthetic compounds based on the definition in the memory circuit, and/or to screen the library of the plurality of synthetic compounds for a particular function.

In accordance with various embodiments, the process of designing and/or screening the library can utilize fewer processing resources and memory resources of the logic circuitry and/or other circuitry than other design techniques or designed libraries. While libraries can be formed of sizes that are defined as a function of (the number of possible molecules at each position)^(number of positions in the compounds), the amount of mapping data generated and/or stored can be a function of the number of molecules used, which is magnitudes less data as compared to mapping to each compound, and/or to each sequence of subgroups forming the molecules. The mapping data identifies the molecule, the position of the molecule in the sequence of the compound, and the sequence of subgroups forming the molecule. The circuitry which analyzes the results from screening the library, which in some embodiments includes the same logic circuitry or the other circuitry in communication with mass spectrometry circuitry, can compare mass spectrometry results to the map that correlates the mass spectrometry characteristics to molecules, positions in the sequence, and the subgroup sequence of the molecules. Similarly to the logic circuitry, the processing resources used by the circuitry analyzing the mass spectrometry results can be reduced as compared to other designed libraries as the circuitry searches and/or compares the known mass spectrometry characteristics of the plurality of possible molecules to the mass spectrometry results. As a specific example, while the library can include $10^{10}$ different compounds, to identify a specific compound that is suspected of a desired function, one hundred different mass spectrometry characteristics (e.g., one hundred molecular weights, one hundred fragmentation patterns, one hundred elution times, one hundred isotope distributions, and/or various combinations thereof) are scanned for.

Figure 6:
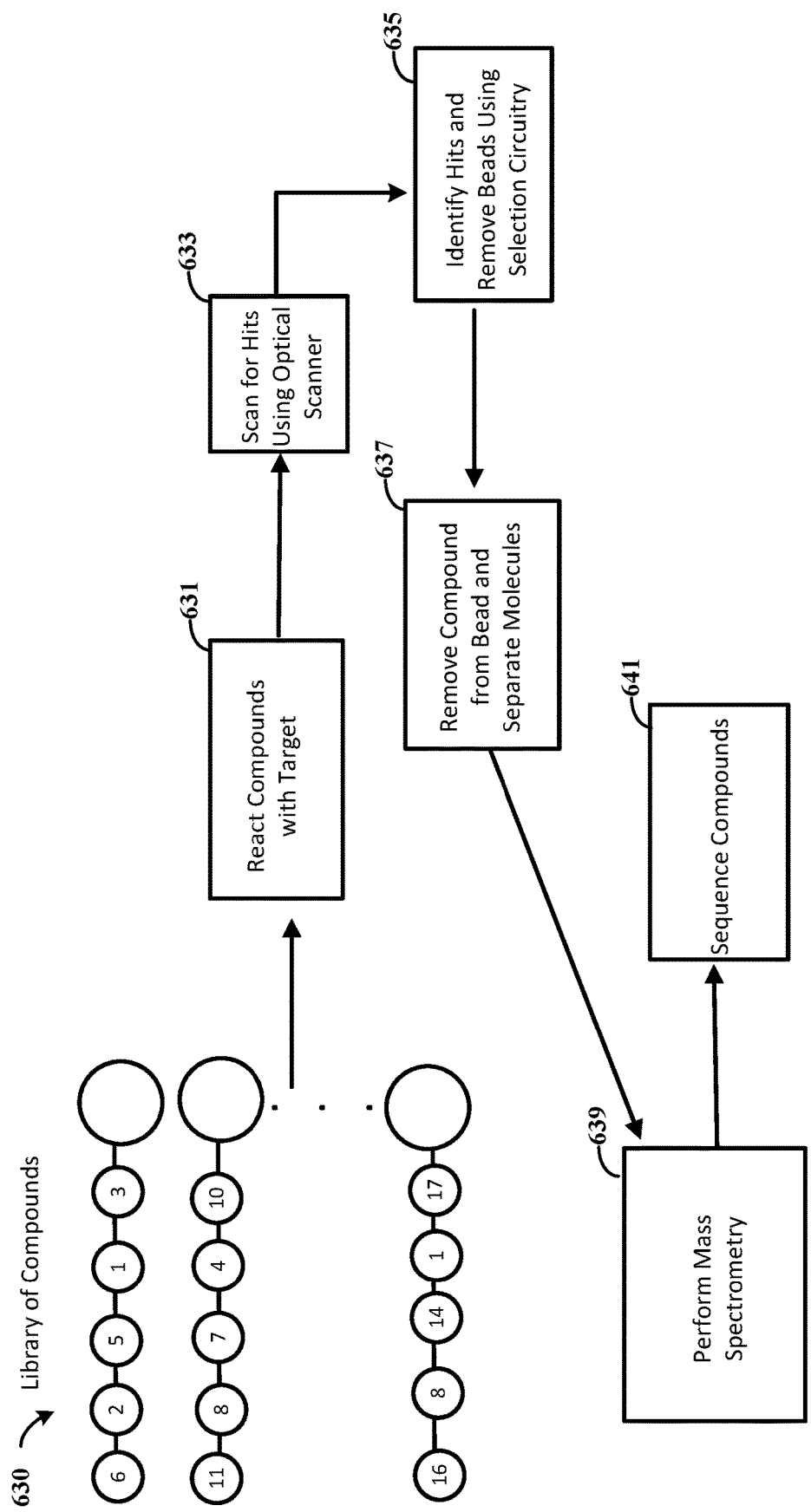
FIG. 6 illustrates an example process for screening a library of a plurality of compounds, in accordance with various embodiments.

FIG. 6 illustrates an example process for screening a library of a plurality of compounds, in accordance with various embodiments. The library 630 can include the library formed using the process illustrated by FIGS. 5A and 5B. The library of compounds, at 631, is reacted with a target, which may be labeled. The compound can be reacted on a screening plate, such as an assay, and non-reacted material is washed away. The screening plate is screened, at 633, for hits using an optical scanner. For example, the screening plate can be scanned to identify compounds that are exhibiting a particular function, such as binding to the labeled target. At 635, hits are identified and the compounds are removed and plated using selection circuitry. Examples of selection circuitry includes a glass capillary (e.g., for manual picking) and/or a capillary extractor for automated picking such as the ALS CellCelector or flow sorting using a fluorescence-activated cell sorting instrument. The compounds that are isolated are cleaved, at 637, to remove the compound from the bead and/or to separate the molecules from one another. The cleavage can be performed via chemical, physical (e.g., temperate), light induced and/or biological/enzymatic methods. The cleavage results in a mixture of the molecules, separated from one another, in solution. The mixture can be used to identify the sequence of the compound (e.g., what order the molecules are in the compound) by performing mass spectrometry, at 639, to identify the mass spectrometry characteristics of the molecules that form the compounds. At 641, the mass spectrometry characteristics are used to sequence the compound including identifying the molecules in the compound, the position of each molecule in the sequence of the compound, and the sequence order of subgroups forming each molecule. For example, the mass spectrometry characteristics map to identification of the molecule, the respective position in the sequence of the compound, and the respective sequence of subgroups, as previously described.

Figure 7:
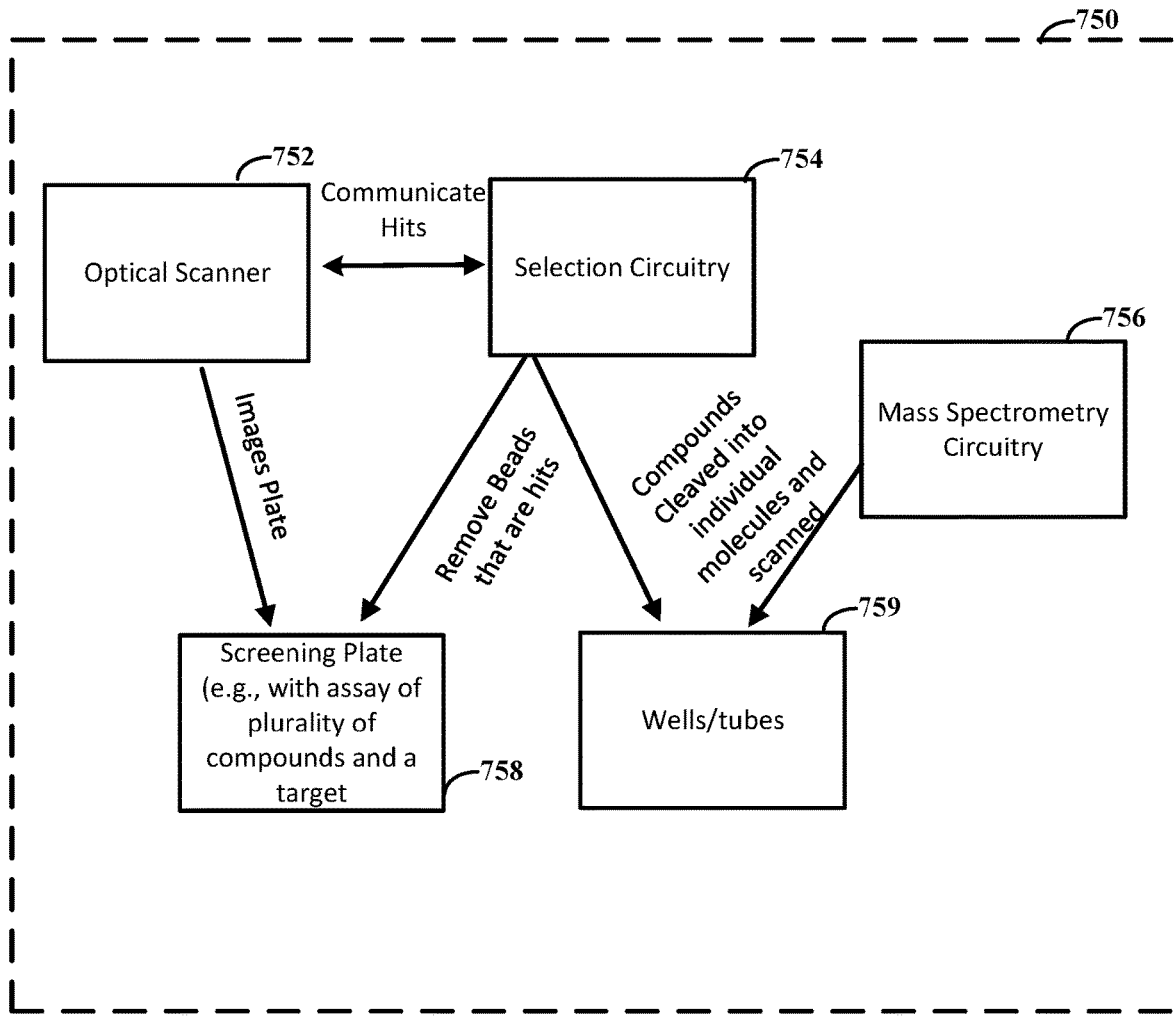
FIG. 7 illustrates an example of a system used to screen a library of a plurality of compounds, in accordance with the present disclosure.

FIG. 7 illustrates an example of a system used to screen a library of a plurality of compounds in accordance with the present disclosure. As illustrated, the system 750 includes an optical scanner 752, a screening plate 758, selection circuitry 754, wells and/or tubes 759, and mass spectrometry circuitry 756. The above-described methods and/or polymer beads can be used to generate a library of 10^8 to 10^9 (or more) compounds. The library can be screened for hits to a target using an optical scanner 752. An example of an optical scanner is a fiber optic scanner, which includes a fiber optic bundle array, a laser, and imaging circuitry (e.g., camera), such as FAST, as previously described. An assay can be performed with the beads to identify compounds on the exhibiting particular function. The assay can be used to bind to a protein, inhibit an enzyme, and/or neutralize or kill a cell, among other functions. The detected activity is assessed via a fluorescent readout of the assay using the optical scanner 752. Identified beads that are suspected of exhibiting the particular function or activity are identified based on the scan and removed from the screening plate 758 and placed in wells or tubes 759 using selection circuitry 754 (e.g., a robot). The removed beads are further processed to cleave the compounds from the beads and, optionally, into individual molecules. The molecules in solution are then read out using mass spectrometry circuitry 756 to identify the molecules, the respective position of each molecule in the sequence of the compound, and the respective sequence of subgroups forming each molecule.

As previously described, circuitry, such as logic circuitry, can be in communication with the mass spectrometry circuitry 756 and can receive the results from the mass spectrometry process. The circuitry can receive or otherwise have the map that identifies the possible molecules at each position in compounds of the library and the respective mass spectrometry characteristics. The map, and/or other data, can also identify the sequence of subgroups forming each of the possible molecules. In response to receiving the results from the mass spectrometry circuitry 756, the circuitry compares the mass spectrometry characteristics in the map to the received results to identify molecules in the compound, the sequence order of the molecules, and the sequence order of subgroups forming the compound.

Embodiments in accordance with the present disclosure include libraries of synthetic compounds, methods of forming such library, and methods of using the libraries to identify new compounds having particular functions. The library can be designed using a mass spectrometry sequencing approach to directly analyze oligomers or polymers without requiring complete mass spectrometry-based fragmentation. The compounds are formed of a plurality of molecules that are designed to be both chemically diverse and easily sequenced through the introduction of cleavable elements along the polymer chain. The molecules can be cleaved and directly read by mass spectrometry analysis from single beads. As previously described, the library can be designed using logic circuitry and stored as data in a memory circuit of the logic circuitry and/or in communication with the logic circuitry. In various embodiments, the designed library can be formed, thus resulting in a library of synthetic compounds that are physically formed.

More Detailed/Experimental Embodiments

As previously described, to screen libraries on the order of 10^8 to 10^9 or more compounds, polymer beads that are sub-ninety microns are used. In various experimental embodiments, the bead sizes include ten micron diameter resin. In order to screen libraries formed using beads of such size, the resulting compounds can be analyzed using mass spectrometry techniques that ionizes the molecules and sorts ions based on their mass-to-charge ratio. The amount of material required to sequence the compounds can be a limitation. As described above, various embodiments include the use of molecules with known and unique (with respect to one another) mass spectrometry characteristics that effectively act as barcodes used to identify the sequence of the compound. In some experimental embodiments, sub-fmol amounts of material can be measured by mass spectrometry. The composition of the library is designed as a sequence of molecules (e.g., cleavable fragments) that have unique mass spectrometry characteristics which can be distinguished from one another via mass spectrometry. A combination of mix-in-split synthesis is used to synthesize the compounds composed of a plurality of the molecules with cleavable groups between at least some of the molecules. After screening and selecting beads having compounds exhibiting particular functions, the selected beads are isolated and cleaved into the molecules. The resulting fragments are analyzed via mass spectrometry to identify the composition of the compound, for example, to sequence the compound.

Figure 8A:
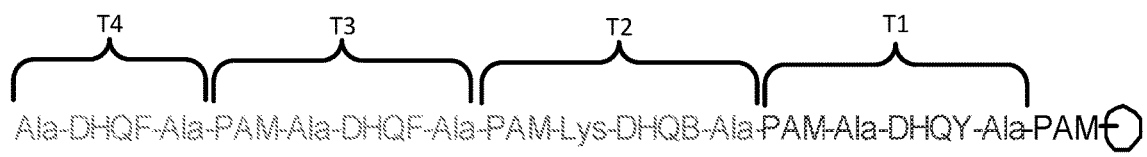
FIGS. 8A-8C illustrate an example of a compound and cleaved molecules of the compound, in accordance with various embodiments.
Figure 8B:
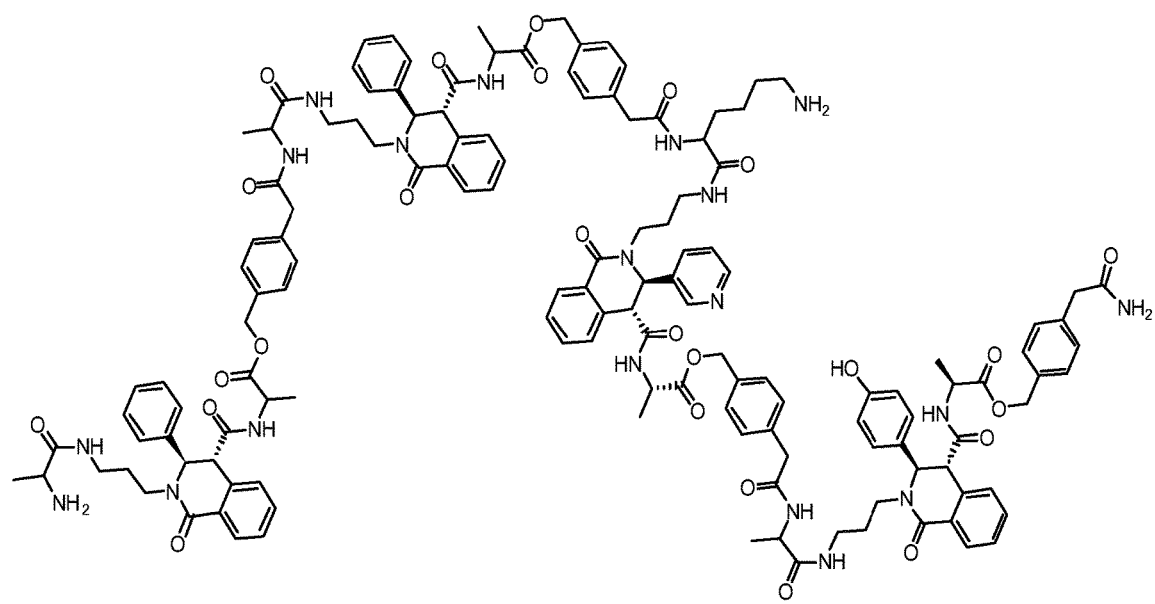
Figure 8C:
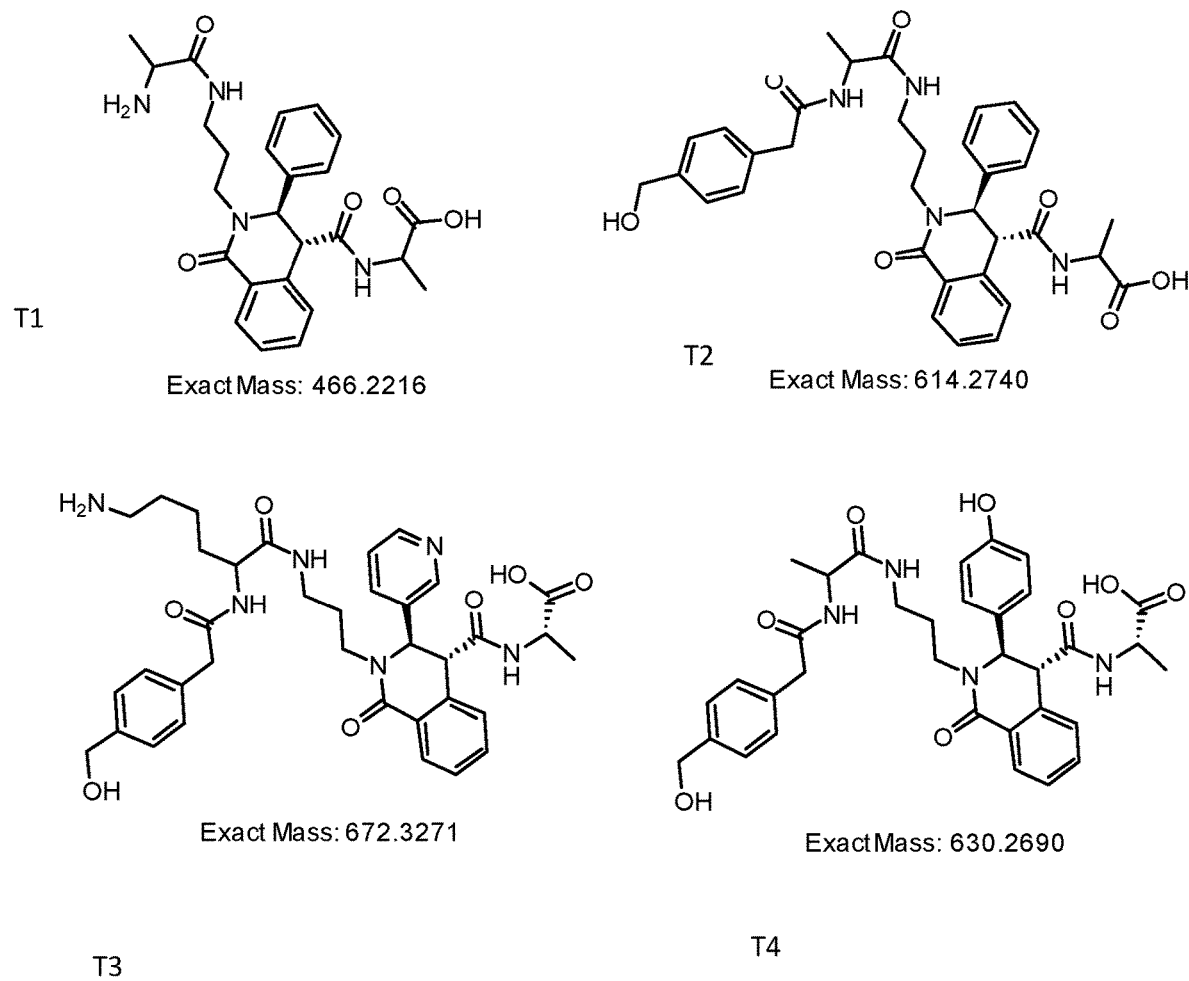

FIGS. 8A-8C illustrate an example of a compound and cleaved molecules of the compound, in accordance with various embodiments. The compound as illustrated by FIG. 8A includes a sequences of four molecules T1-T4. The four molecules T1-T4 can include a plurality of subgroups (e.g., four subgroups each). A cleavable group can be used to attach the compound to the bead and couple to the first molecule T1. The first molecule T1 can include a sequence of subgroups Ala-DHQY-ALA-PAM. The second molecule T2 can include a sequence of subgroups Ala-DHQB-LYS-PAM, the third molecule T3 can include a sequence of subgroups ALA-DHQF-ALA-PAM, and the fourth molecule T4 can include a sequence of subgroups ALA-DHQF-ALA. As illustrated, the plurality of molecules T1-T4 include cleavable groups. More specifically, the cleavable groups, e.g., PAM, can be located between at least some of the molecules T1-T4 and used to connect the molecules T1-T4 together.

The compound attached to the bead can be placed in contact with a first cleavage solution. The first cleavage solution can include trifluoroacetic acid (TFA), which cleaves the compound from the bead, as illustrated by FIG. 8B. The compound can further be placed in contact with a second cleavage solution, such as NaOH, which cleaves the molecules from one another, as illustrated by FIG. 8C.

As may be appreciated, embodiments are not limited to the number of molecules, subgroups, chemical cleavages, or to the specific subgroups illustrated by FIG. 8A-8C. Rather, FIGS. 8A-8C are provided for illustrative, and not limiting, purposes. Further, the cleavage can include other types of methods, such as physical (e.g., temperate), light induced and/or biological/enzymatic method and/or other solutions than described.

Figure 9A:
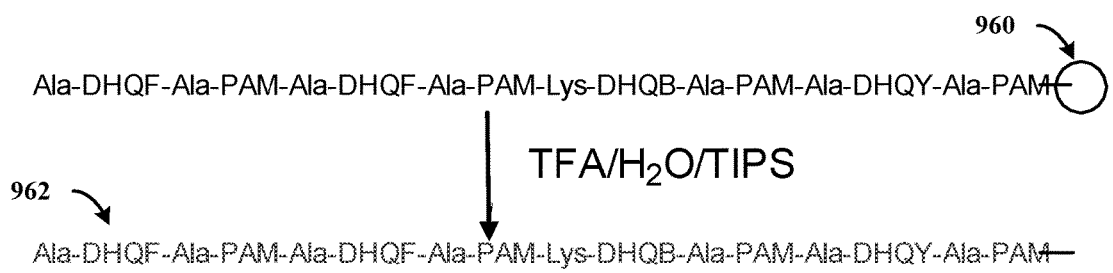
FIGS. 9A-9C illustrate an example of a compound and resulting mass spectrometry characteristics of the compound as cleaved from the bead, in accordance with various embodiments.
Figure 9B:
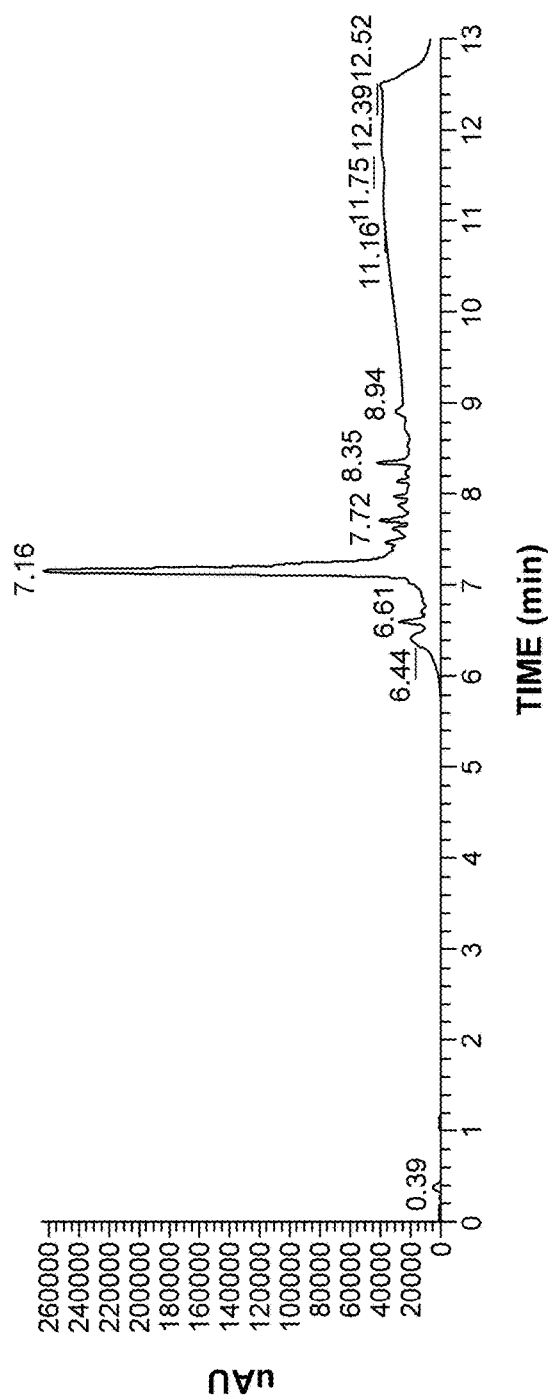
Figure 9C:
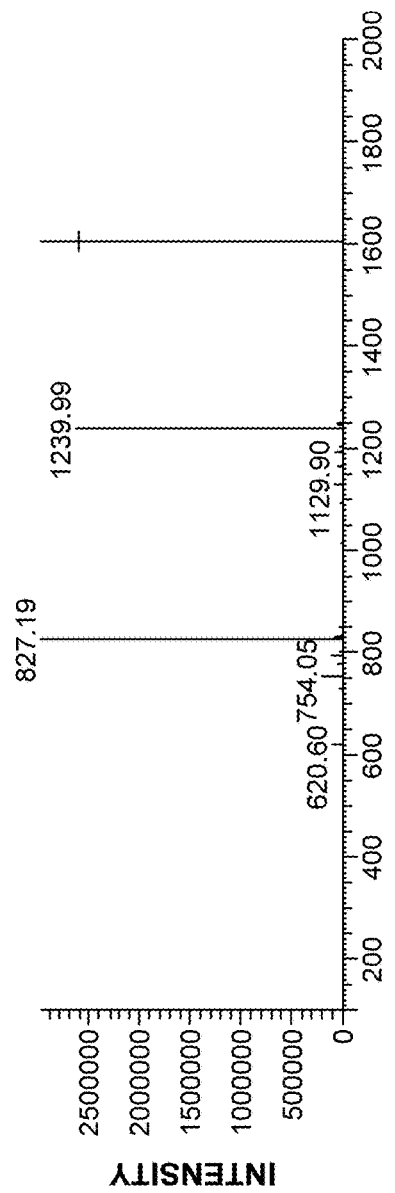

FIGS. 9A-9C illustrate an example of a compound and resulting mass spectrometry characteristics of the compound cleaved from the bead, in accordance with various embodiments. As illustrated by 9A, a compound 962 can be cleaved from a bead 960 using a cleaving solution, such as a solution including TFA. FIG. 9B illustrates an example high-performance liquid chromatography (HPLC) analysis of the cleaved compound illustrated in FIG. 9A. The HPLC results illustrate purity of the component in mixture. FIG. 9C illustrates example mass spectrometry results of the cleaved compound illustrated in FIG. 9A. As illustrated, the mass spectrometry results show expected patterns that correctly identifies the compound.

Figure 10A:
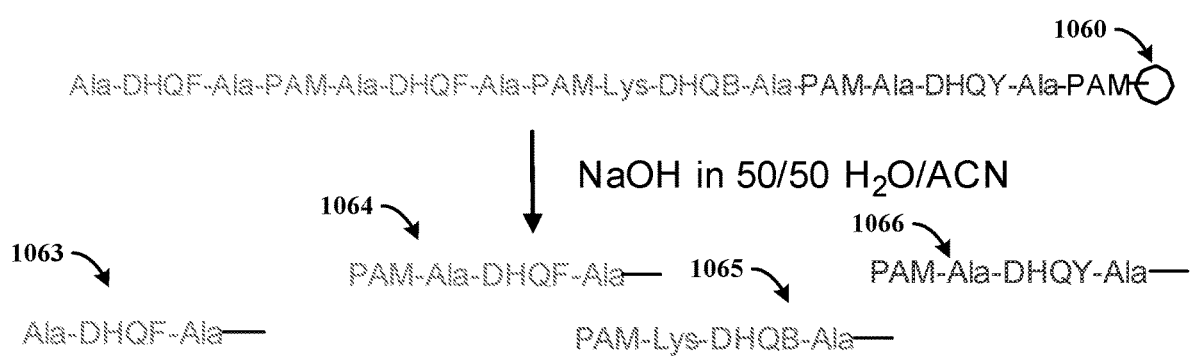
FIGS. 10A-10C illustrate an example of a compound and resulting mass spectrometry characteristics of the molecules as cleaved from one another and the bead, in accordance with various embodiments.
Figure 10B:
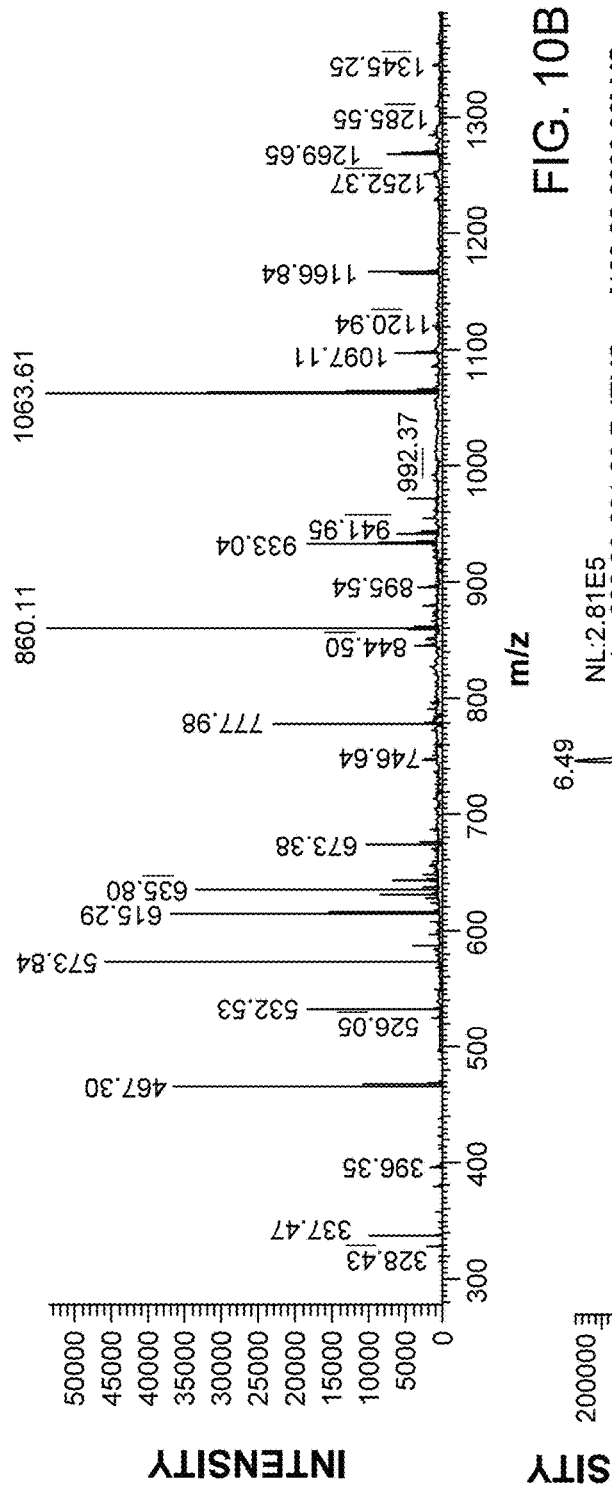
Figure 10C:
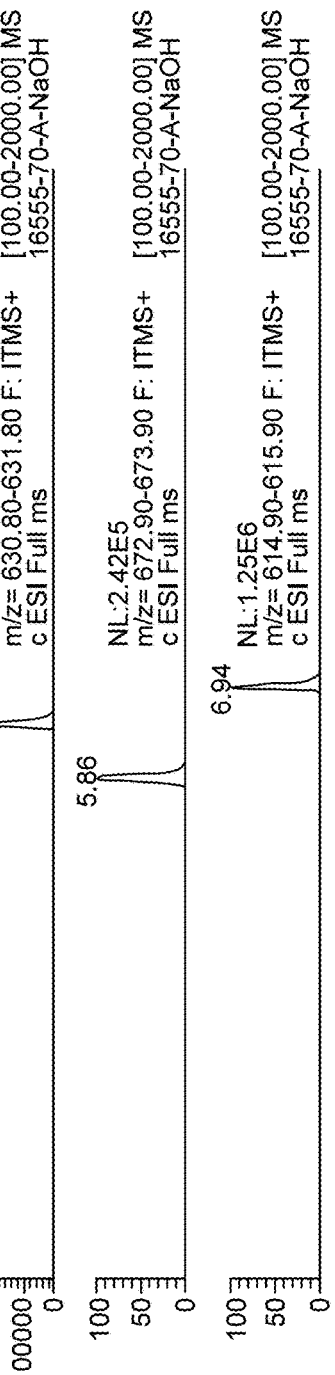

FIGS. 10A-10C illustrate an example of a compound and resulting mass spectrometry characteristics of the compound cleaved from the bead, in accordance with various embodiments. As illustrated by FIG. 10A, the compound can be cleaved from a bead 1060 and into individual molecules 1063, 1064, 1065, 1066 using a cleaving solution, such as a solution including NaOH. FIGS. 10B-10C illustrate example mass spectrometry results of the cleaved molecules illustrated in FIG. 10A. As illustrated, the mass spectrometry results show expected patterns that correctly identifies the compound.

Figure 11:
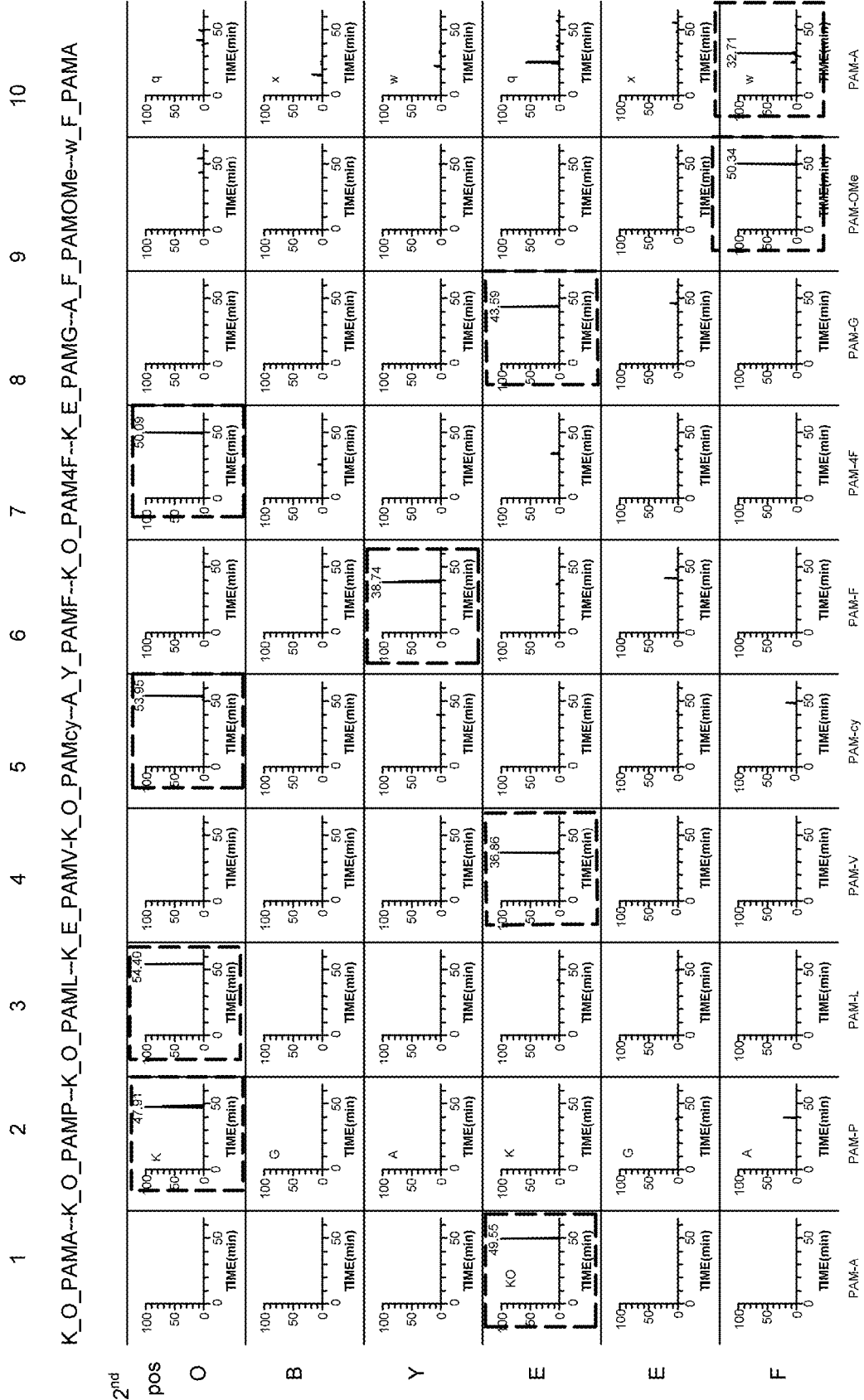
FIG. 11 illustrates an example mass spectrometry characteristics of a compound having six molecules, in accordance with various embodiments.

FIG. 11 illustrates an example mass spectrometry characteristics a compound having ten molecules, in accordance with various embodiments. The library including the compound is designed such that at each of the ten positions there are six possible molecules. The graph illustrates the different possible molecules at the y-axis, and the position in the sequence of the compound at the x-axis. While the library can include $6^{10}$ possible compounds, the mass spectrometry results are checked for sixty (six times ten) different mass spectrometry characteristics, e.g., molecular weights in the experimental embodiment. Using the mass spectrometry results, a molecule is identified at each position in the sequence of the compound.

Figure 12:
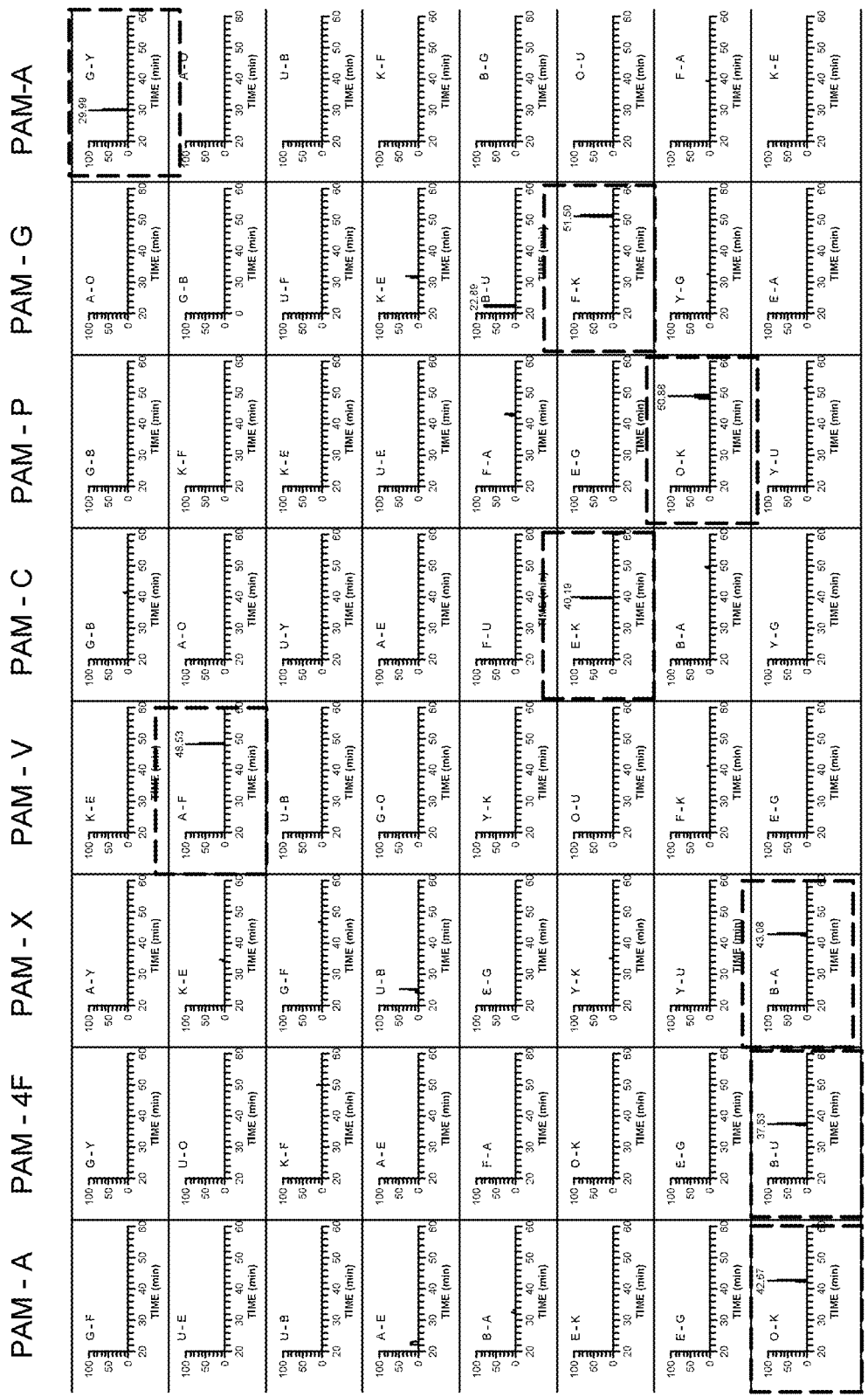
FIG. 12 illustrates example mass spectrometry characteristics of a compound having eight molecules and as cleaved from a ten micron bead, in accordance with various embodiments.
Figure 14A:
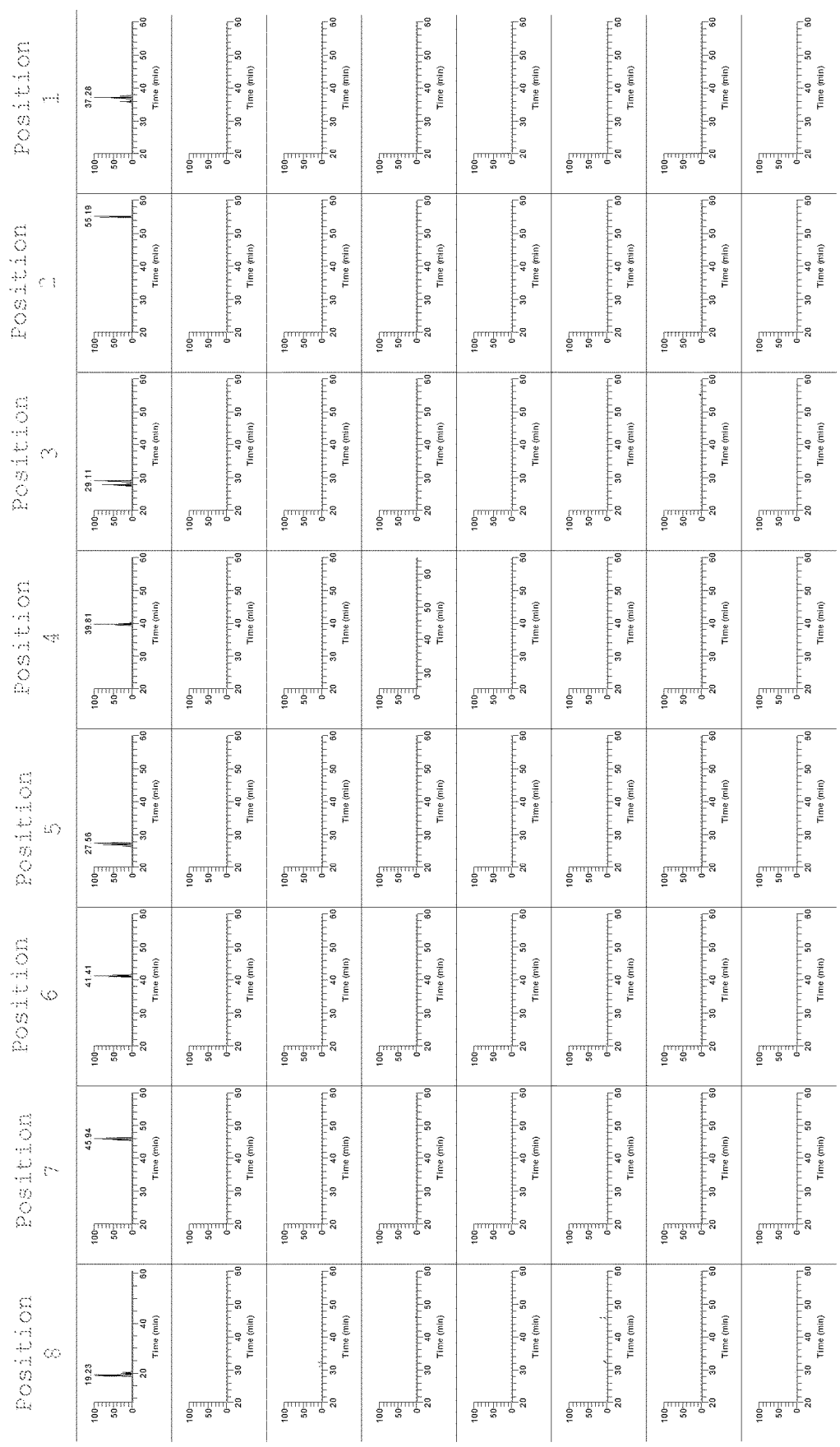
FIGS. 14A-14H illustrate example mass spectrometry results from the set of compounds illustrated by FIGS. 13A-13B, in accordance with various embodiments.
Figure 14B:
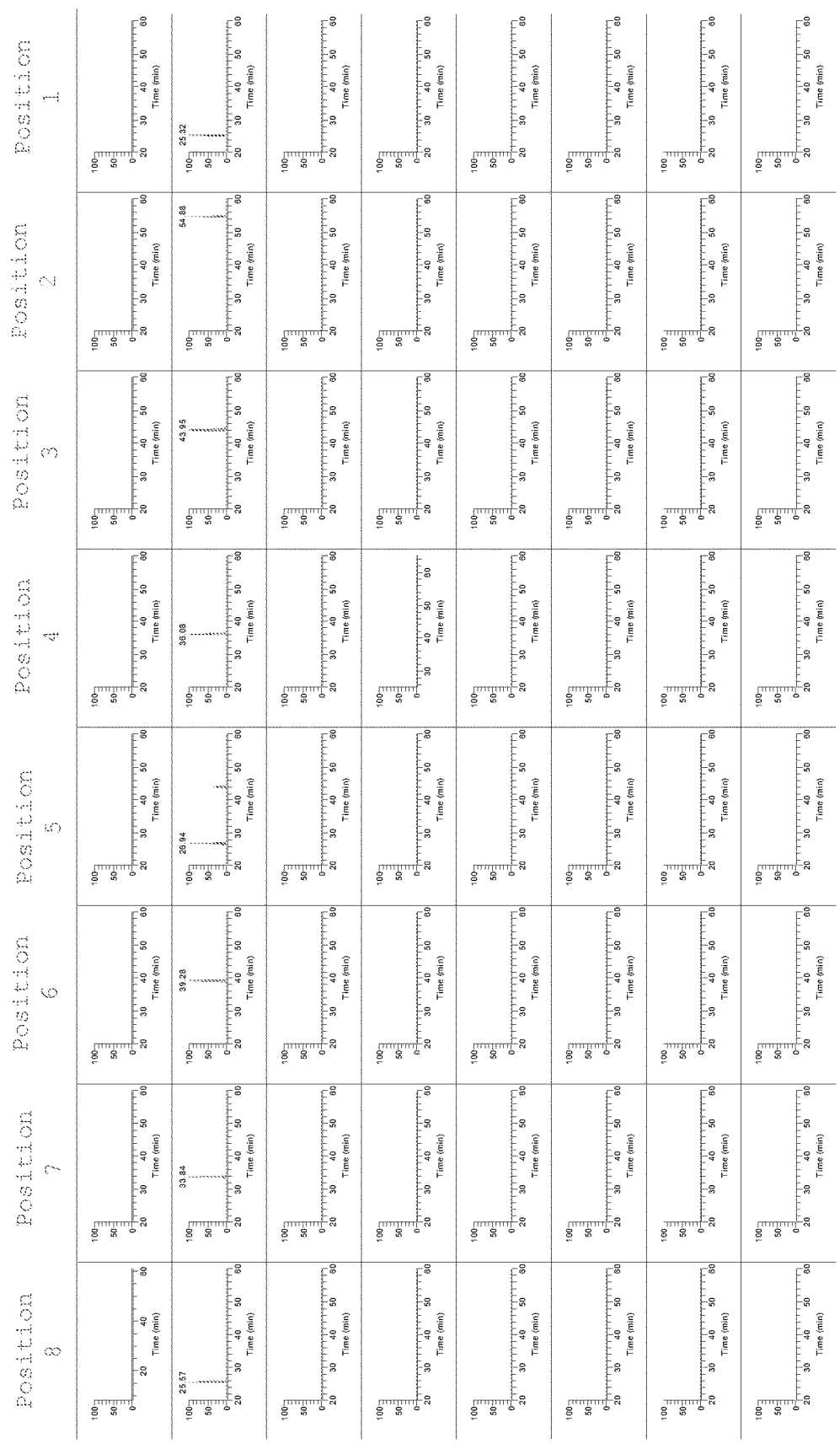
Figure 14C:
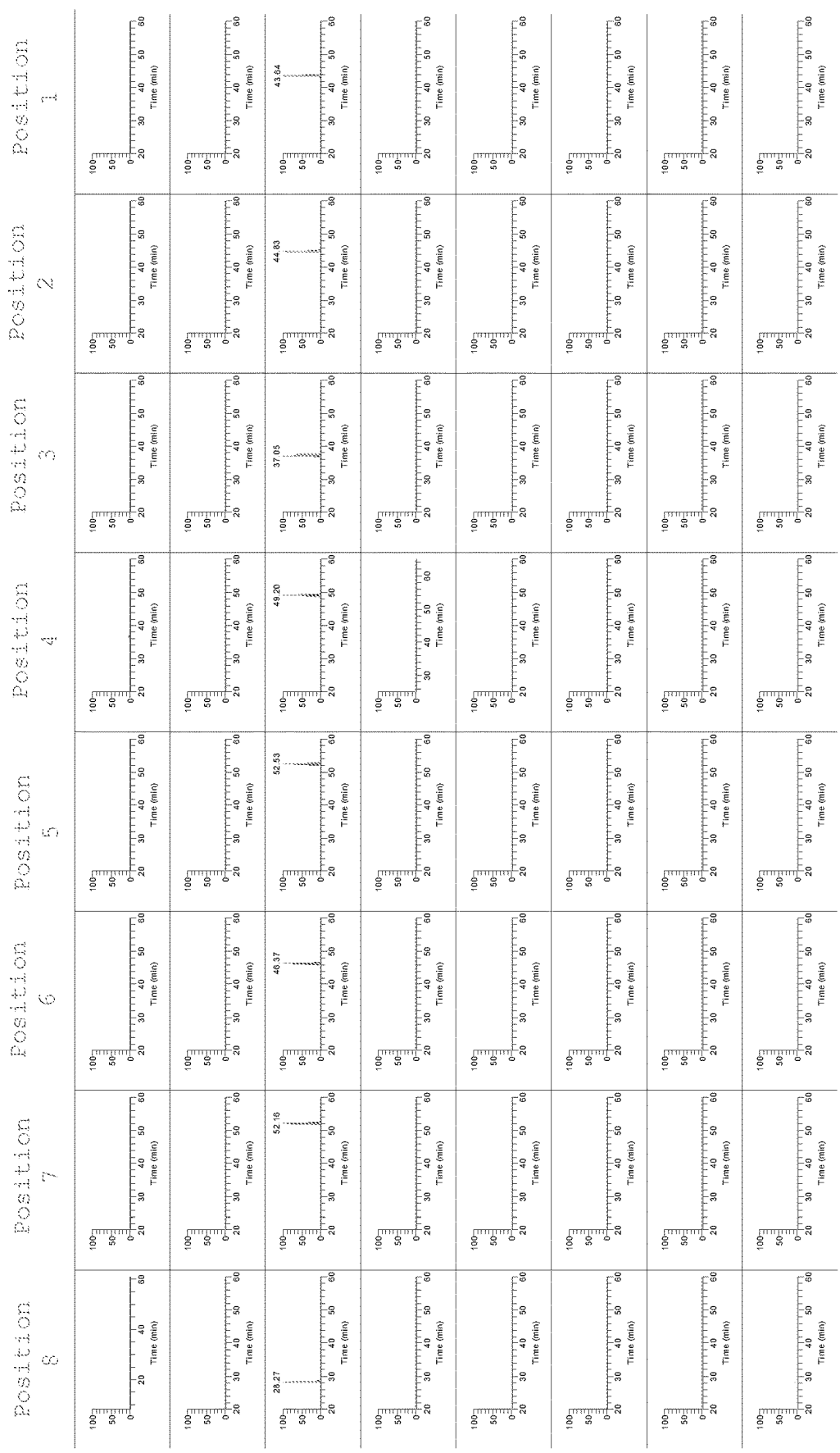
Figure 14D:
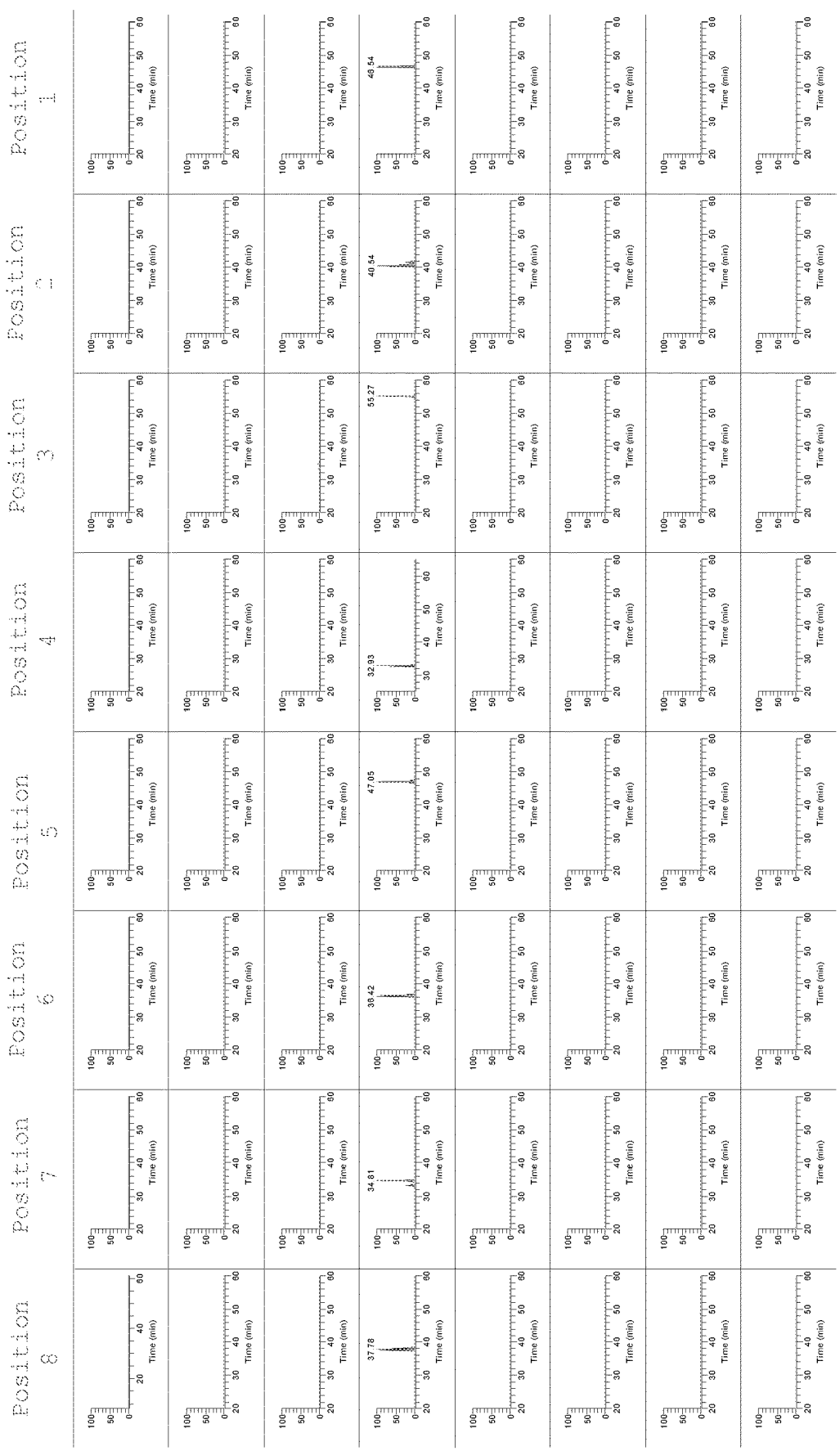
Figure 14E:
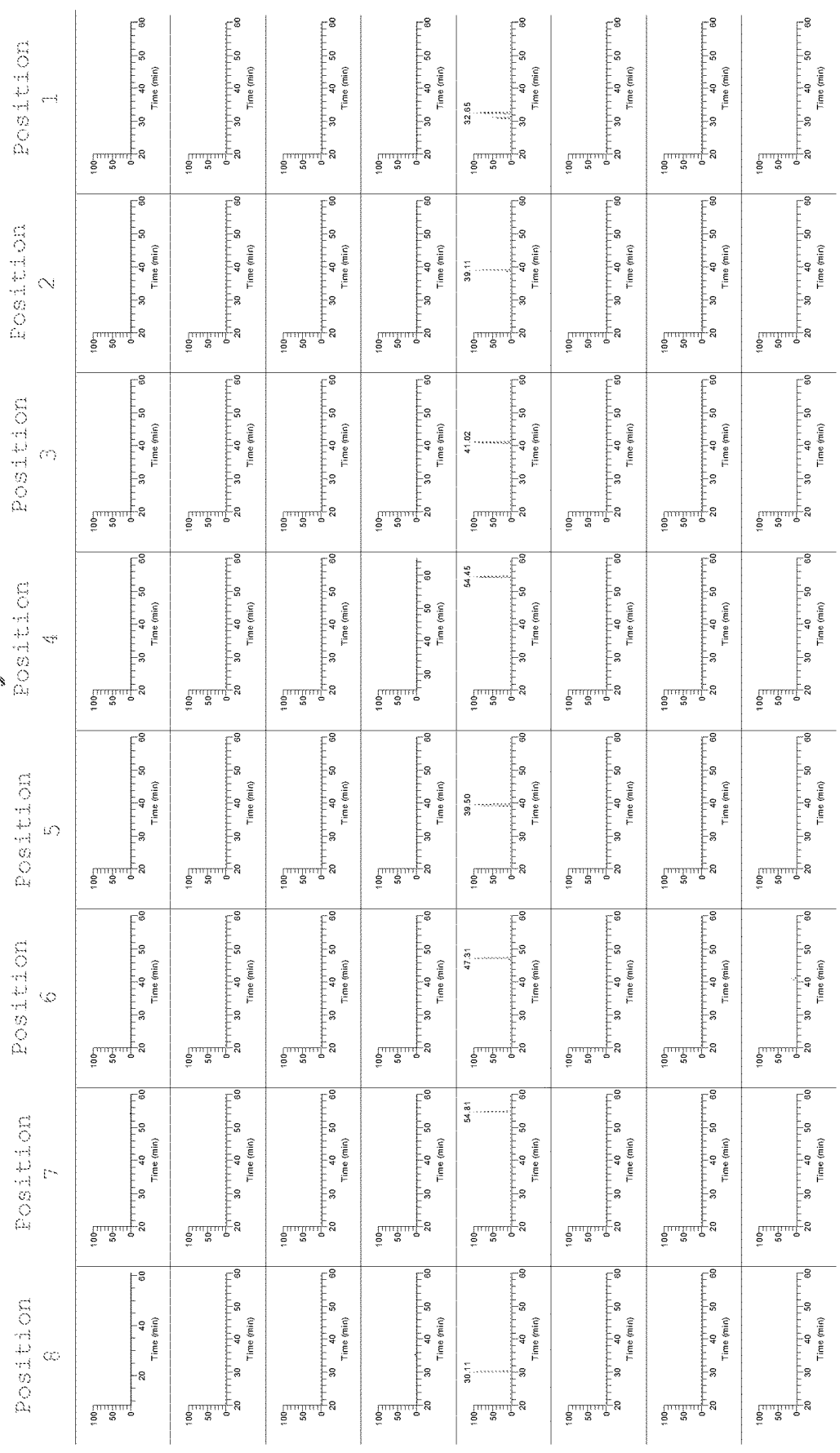
Figure 14F:
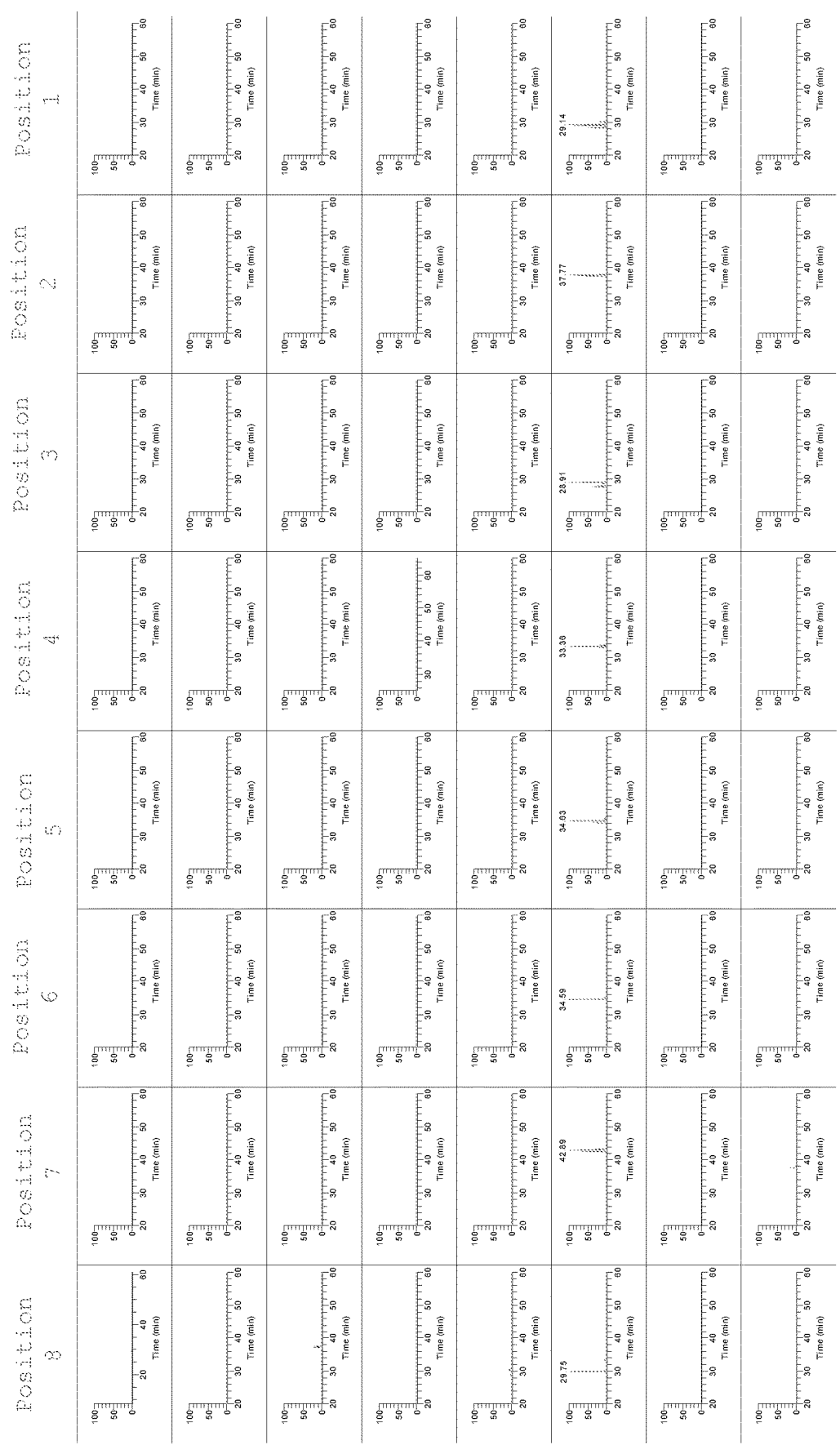
Figure 14G:
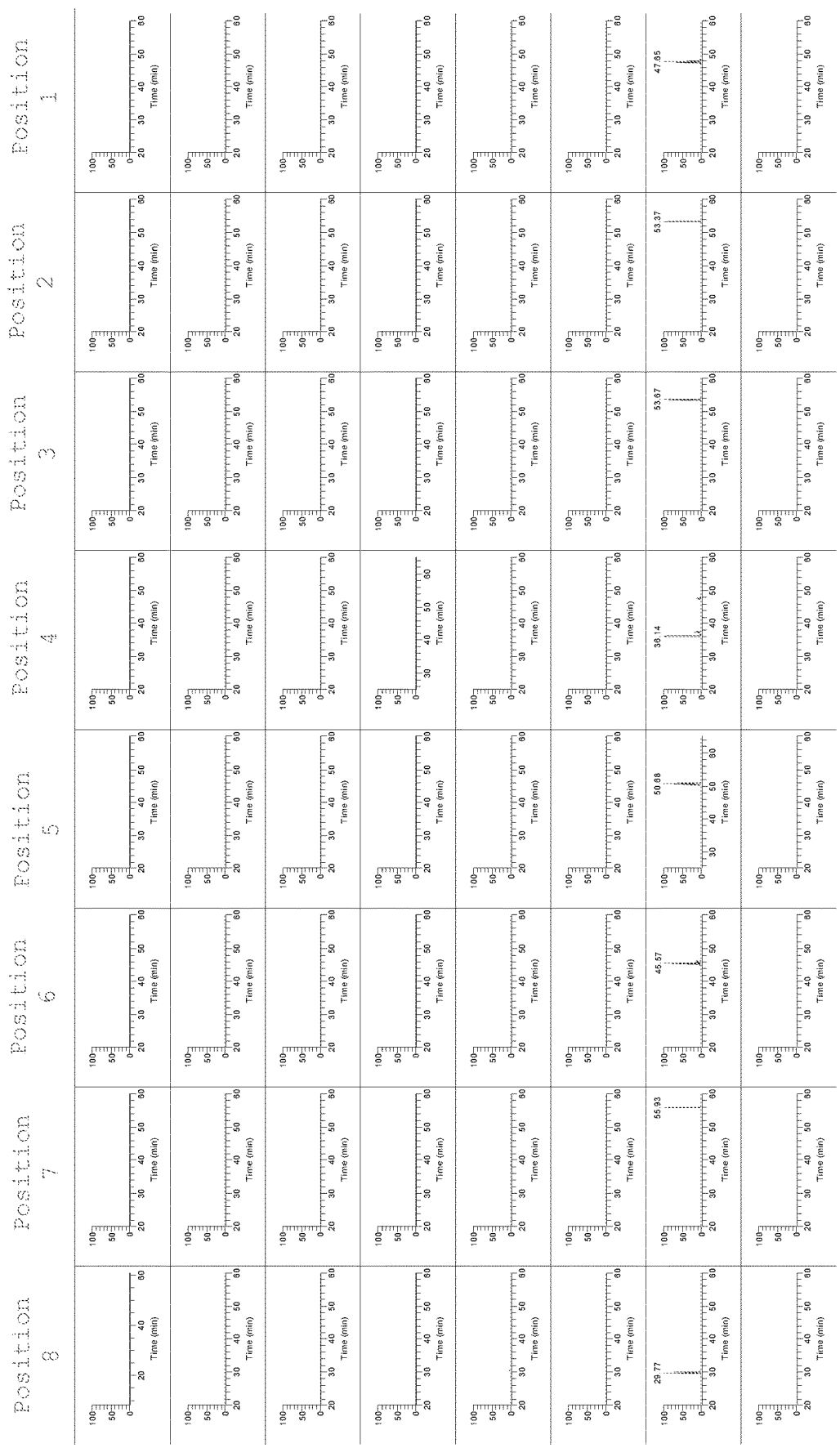
Figure 14H:
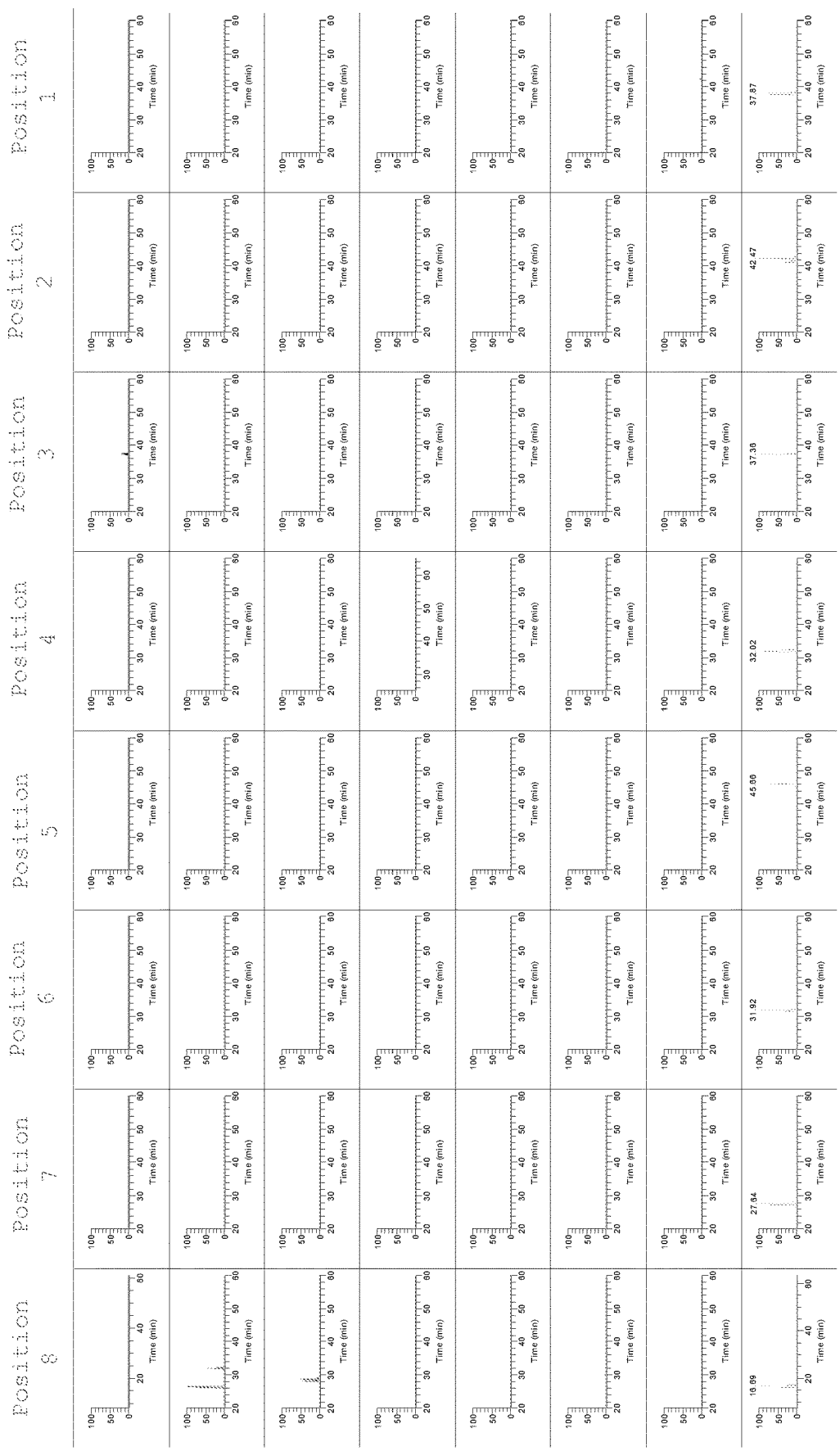

FIG. 12 illustrates example mass spectrometry characteristics of a compound having eight molecules and as cleaved from a ten micron bead, in accordance with various embodiments. Similarly to FIG. 11, the library resulting in the compound is designed, such that at each of the eight positions there are eight possible molecules. The graph illustrates the different possible molecules at the y-axis, and the position in the sequence of the compound at the x-axis. While the library can include $8^8$ possible compounds, the mass spectrometry results are checked for sixty-four (eight times eight) different mass spectrometry characteristics, e.g., molecular weights in the experimental embodiment. Using the mass spectrometry results, a molecule is identified at each position in the sequence of the compound.

FIGS. 13A-13B illustrate an example of a set of compounds formed of eight molecules, in accordance with various embodiments. More specifically, FIG. 13A illustrates an example set of compounds 1370, 1372, 1374, 1376, 1378, 1380, 1382, 1384 and that can be designed using a set of molecules that each include four subgroups. The resulting compounds can include eight molecules in sequence. As illustrated, each of the molecules can be assigned to one of the eight positions in the sequence order of the compounds. The molecular weights, or other mass spectrometry characteristics, of the plurality (e.g., 64) of molecules is known and distinguishable from one another. Although the embodiment of FIG. 13A illustrates eight molecules, the molecules can be used to form a library of $8^8$ possible compounds. The set of eight compounds can be used to illustrate the sequence-ability of the compounds. For example, as illustrated by FIG. 13B, eight compounds are synthesized from the plurality of molecules (e.g., sixty four total molecules). The eight compounds synthesized can encompass each of the plurality of possible molecules.

FIGS. 14A-14H illustrate example mass spectrometry results from the set of compounds illustrated by FIGS. 13A-13B, in accordance with various embodiments. More specifically, FIGS. 14A-14H illustrate that the mass spectrometry results of each of the tested compounds identifies the correct sequence of the respective compounds. In various embodiments, such a process can be performed to identify control information. For example, the mass spectrometry results can verify the molecular weight, as well as provide a reference point for the fragmentation pattern, elution time, and/or the isotope distribution (e.g., a time window for when the mass spectrometry results are expected). Such values can be used to mitigate false positives. For example, a reference that includes the fragmentation pattern, elution time, and/or isotope distribution for each molecule can be stored. The resulting mass spectrometry characteristics can be compared to the reference to verify the correct pattern.

FIGS. 15A-15D illustrate example mass spectrometry characteristics of two molecules having non-distinguishable molecular weights that are distinguished by other mass spectrometry characteristics, in accordance with various embodiments. As previously described, in various embodiments, the mass spectrometry characteristics used to distinguish the molecules and/or subgroups in the library from another are the same characteristics (e.g., all are distinguished by a molecular weight, fragmentation pattern, elution time and/or isotope distribution) or a subset of the molecules may include non-distinguishable first mass spectrometry characteristics and a second mass spectrometry characteristic that is distinguishable. As an example, multiple molecules in the library can have the sample subgroup composition but with different atom connectivity (e.g., different sequence order of subgroups). In such instances, two or more molecules may have the same molecular weight and/or molecular weights within a threshold of one another, and/or that are otherwise not distinguishable from one another. The molecules can be distinguished using tandem mass spectrometry techniques including, but not limited to, collisionally-activated dissociation, surface-induced dissociation, electron-transfer dissociation, photodissociation, and ion-molecule reaction chemistry.

Figure 15A:
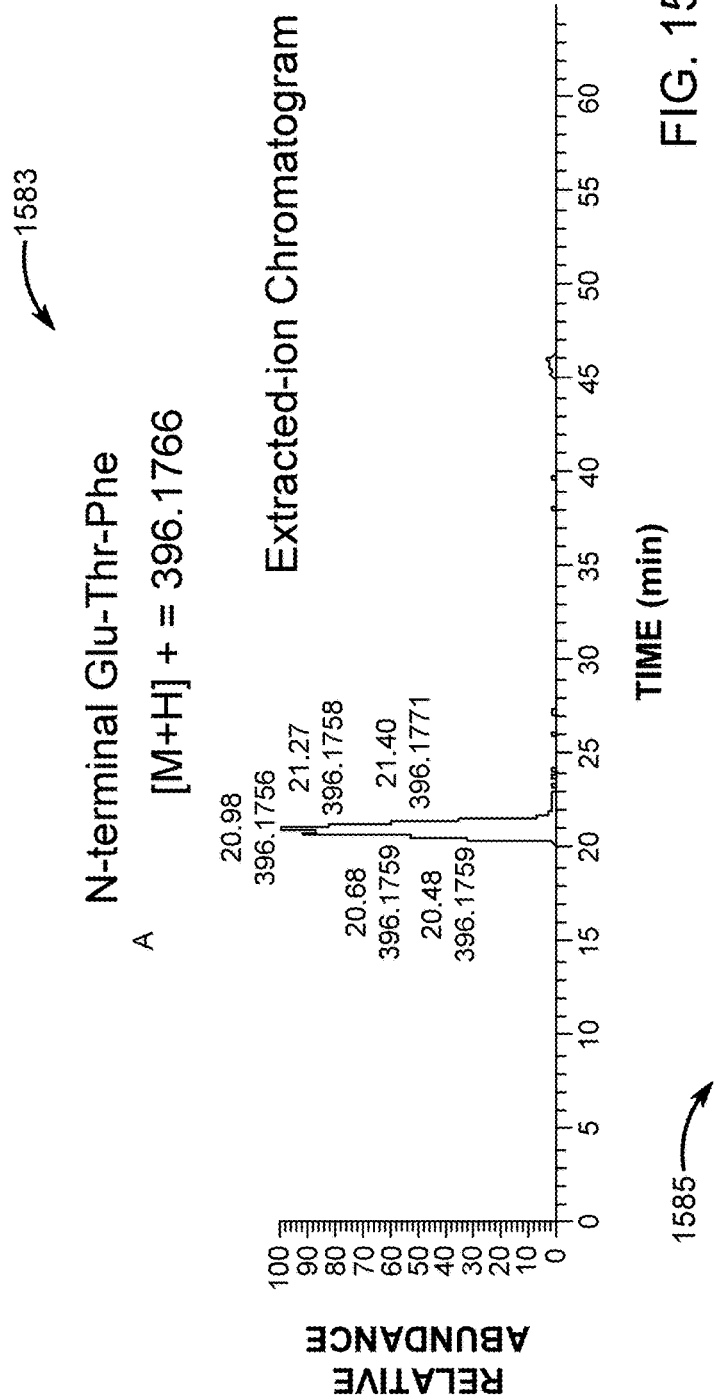
FIGS. 15A-15D illustrate example mass spectrometry results of two molecules having non-distinguishable molecular weights that are distinguished by other mass spectrometry characteristics, in accordance with various embodiments.
Figure 15B:
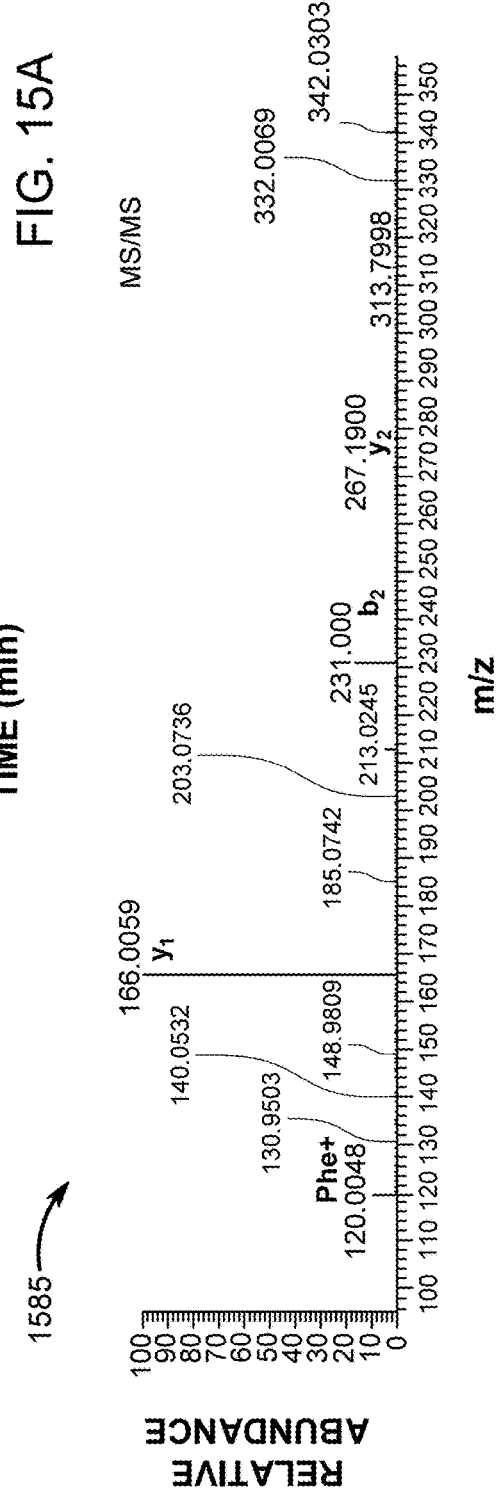
Figure 15C:
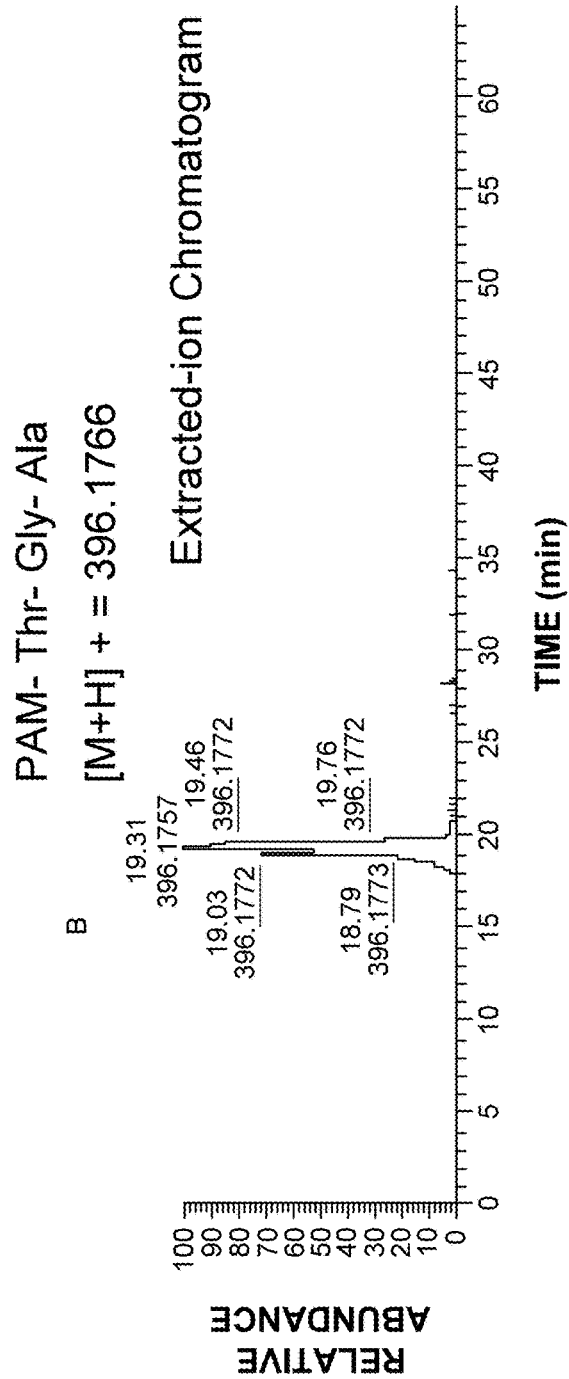
Figure 15D:
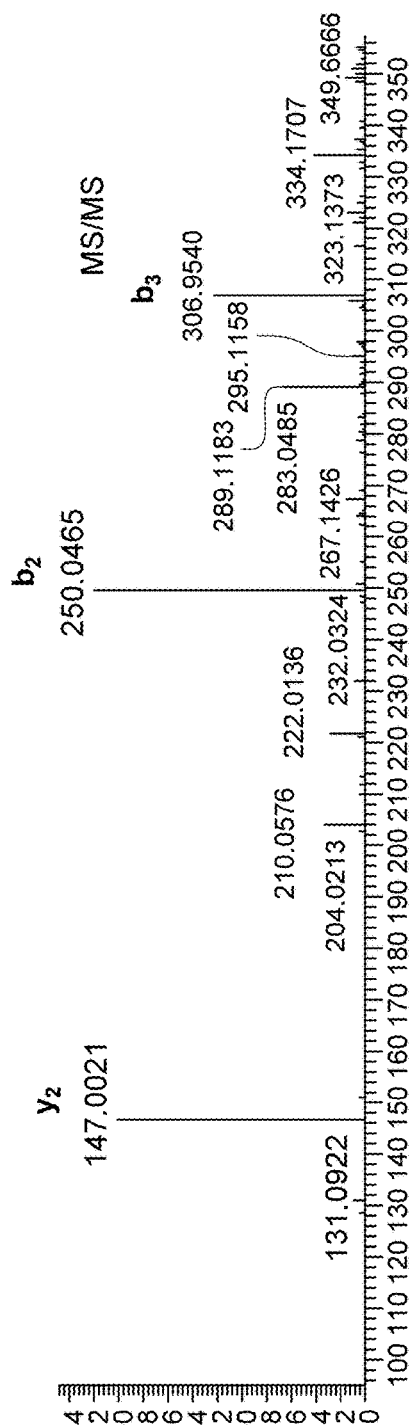

More specifically FIG. 15A and FIG. 15C illustrate two molecules having the same subgroup composition, e.g., the same molecular weight as illustrated by the graphs 1583 and 1587 respectively. As illustrated by FIGS. 15B and 15D, the two molecules can be distinguished based on collisional dissociation as illustrated by the graphs 1585 and 1589.

In various embodiments, more than one mass spectrometry characteristic can be measured in a mass spectrometer, and when appropriately weighted can, in addition, be used to assign statistical confidence levels to the compound sequencing data. For example, in cases where the sequence analysis is performed using coupled liquid-chromatography and mass spectrometry along with tandem mass spectrometry (LC-MS and LC-MS/MS), the data acquired for each potential molecule that is detected, can include chromatographic retention time, accurate measured-mass, and ion fragmentation patterns. Each of these measurements can be used to derive an algorithm that can be used to assign statistical significance to each molecule assignment.

Figure 16:
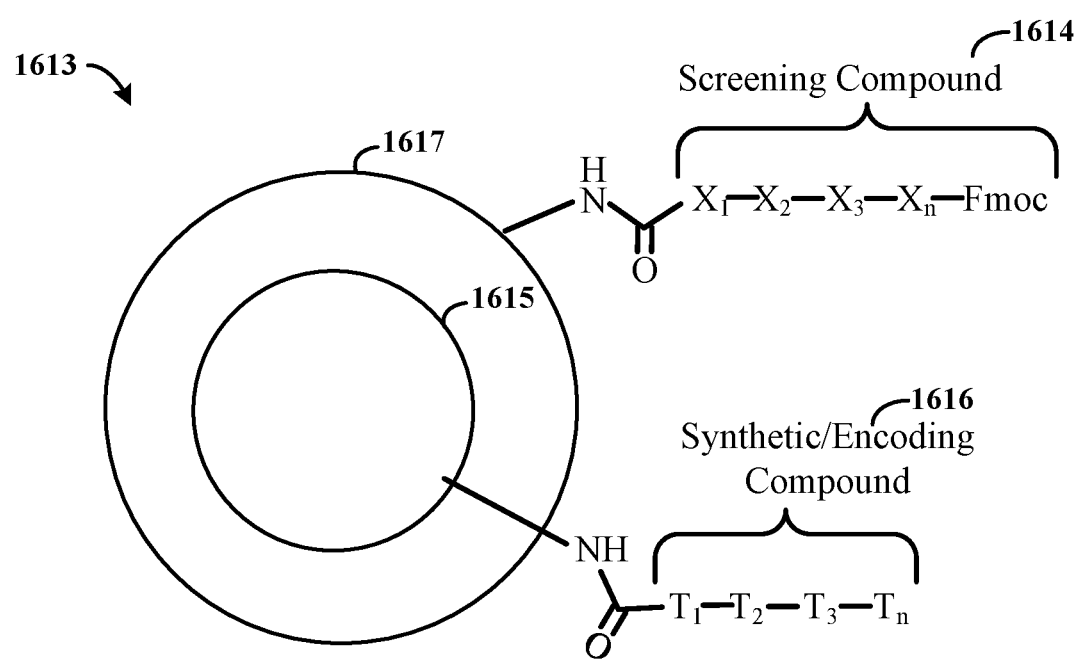
FIG. 16 illustrates an example of a topologically segregated polymer bead, in accordance with various embodiments.

FIG. 16 illustrates an example of a topologically segregated polymer bead, in accordance with various embodiments. In various embodiments, the above described compounds can be used as synthetic encoding compounds. The molecules forming the synthetic encoding compounds can act as barcodes to identify screening compounds. The synthetic encoding compounds are formed of subsets of the plurality of molecules with unique mass spectrometry characteristics and are located on an interior of beads in the library. The screening compounds, which are also synthetic, are located on the exterior of the beads. Each of the mass spectrometry characteristics of the synthetic encoding compounds can map to the screening compound and can be used to sequence a screening compound that exhibits a particular function responsive to screening of the library.

The synthetic encoding compounds and screening compounds can be coupled to a topological segregated polymer bead. FIG. 16 illustrates an example of a topologically segregated polymer bead, in accordance with various embodiments. The polymer bead 1613 is topologically segregated via selective coupling of a screening compound 1614 in the exterior surface 1617 and an encoding compound 1616 in the interior surface 1615. In specific embodiments, the screening compound 1614 is coupled to a deprotected group (e.g., a first functional group/NH) and the interior surface 1615 includes another deprotected group (e.g., a second functional group/NH) coupled to the encoding compound 1616. The encoding compound 1616 is used to label the screening compound 1614. For example, when a library of a plurality of polymer beads are screened, if the screening compound is a hit, the encoding compound 1616 is used to identify the respective sequence of the screening compound 1614. The molecules that form the encoding compound are identified using mass spectrometry, as described above. Each encoding compound can map to a specific screening compound. Thereby, the identification of the encoding compound identifies the sequence of the screening compound.

Figure 17:
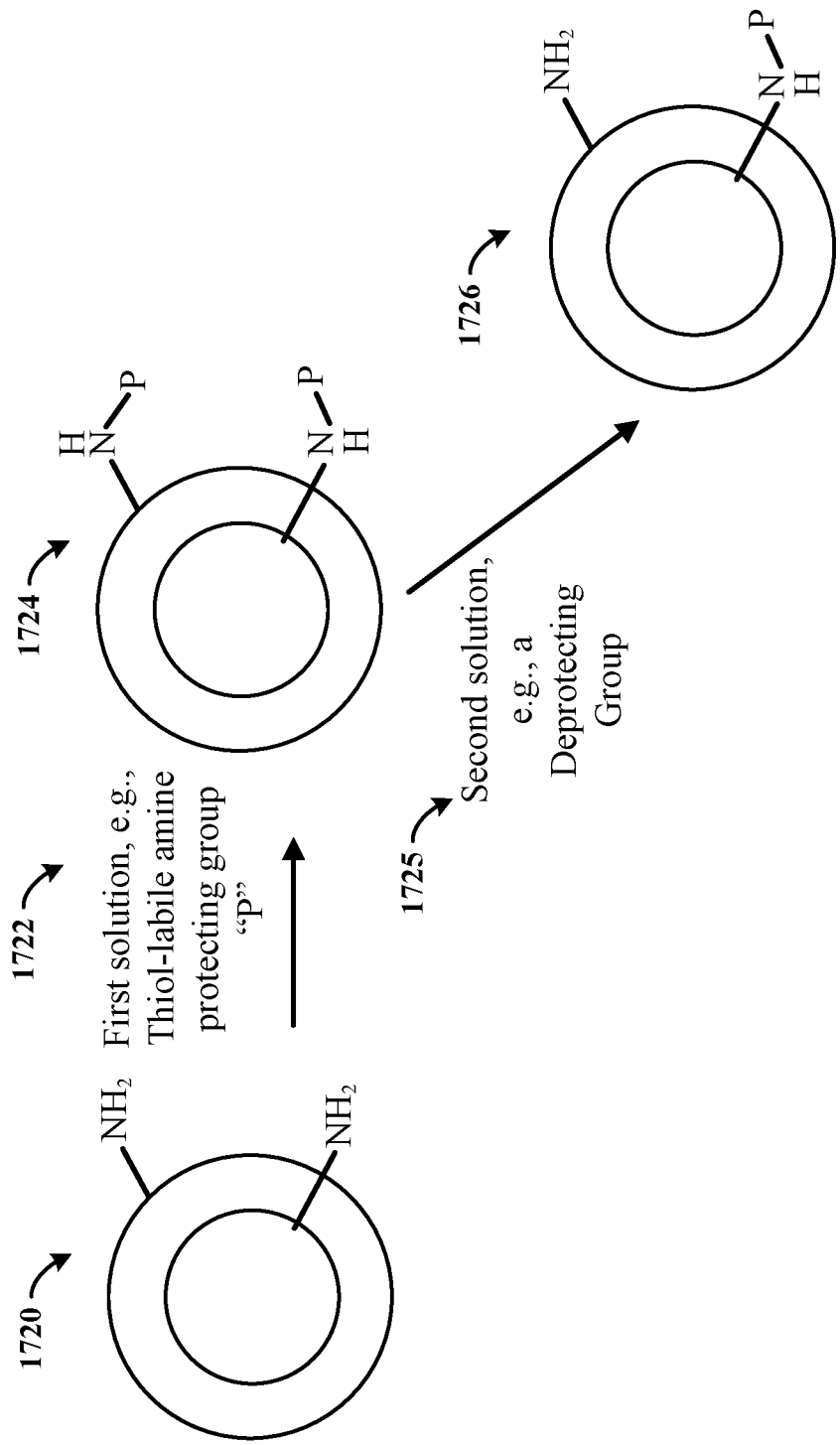
FIG. 17 illustrates an example process for topologically segregating a polymer bead, in accordance with various embodiments.

FIG. 17 illustrates an example process for topologically segregating a polymer bead, in accordance with various embodiments. A starting polymer bead 1720 can include M-NH$_2$ Tentagel beads. The polymer beads 1720 are caused to contact a first solution at 1722. The first solution can include a thiol-labile amine protecting group, which is labelled "P". The protecting group can include 2-4-Dinitrobenzenesulfonamides (DNs) and/or 2-nitrobenzenesulfonamide (Ns). In specific embodiments, the first solution includes the protecting group (e.g., DNs-chloride or DNs-CL, or Ns-chloride or Ns-Cl), N,N-diisopropylethylamine (DIPEA), and dichorlmethane (DCM). By contacting the bead 1720 with the first solution, the resulting bead 1724 is formed which includes a protecting group (e.g., P) in the interior and exterior surfaces. Contacting the polymer bead 1720 with the first solution can include reacting the polymer bead with the protecting group, whereby the protecting group can deprotect in the presence of thiols.

The polymer bead 1724 is then caused to contact a second solution at 1725. The second solution can include a deprotecting group, such as a protein having cysteines that selectively deprotect surface amines without deprotecting interior amines. The protein can be of a size that it cannot penetrate the pores of the polymer bead 1724 to deprotect interior amines (e.g., bovine serum albumin (BSA)). The contact with the second solution at 1725 results in the topologically segregated polymer bead 1726, which can be referred to as "bead shaving". The topologically segregated polymer bead 1726 includes a deprotected group in the exterior surface (e.g., NH$_2$) and a protecting group in the interior surface.

Figure 18A:
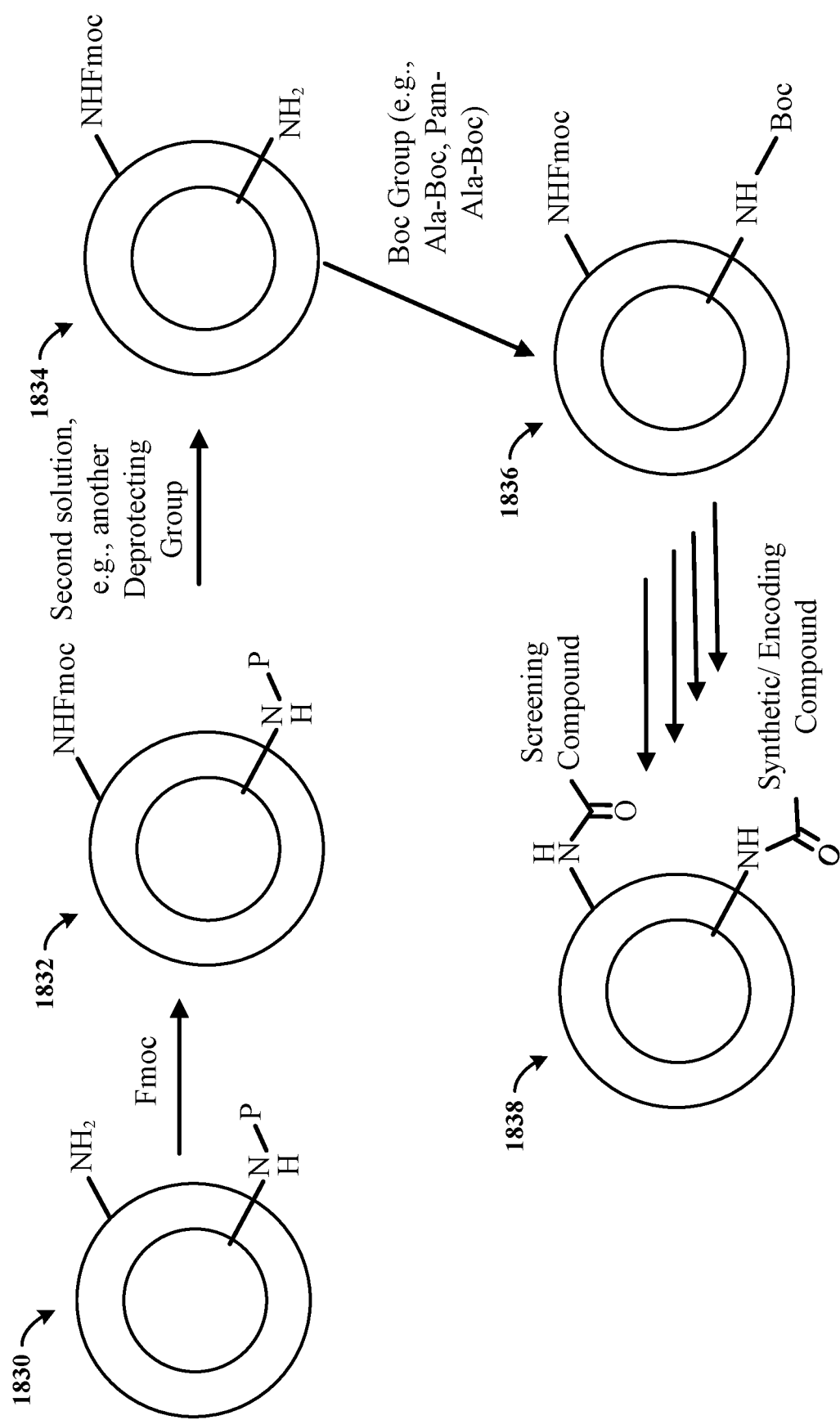
FIGS. 18A-18B illustrate an example process for topologically segregating a polymer bead, in accordance with various embodiments.
Figure 18B:
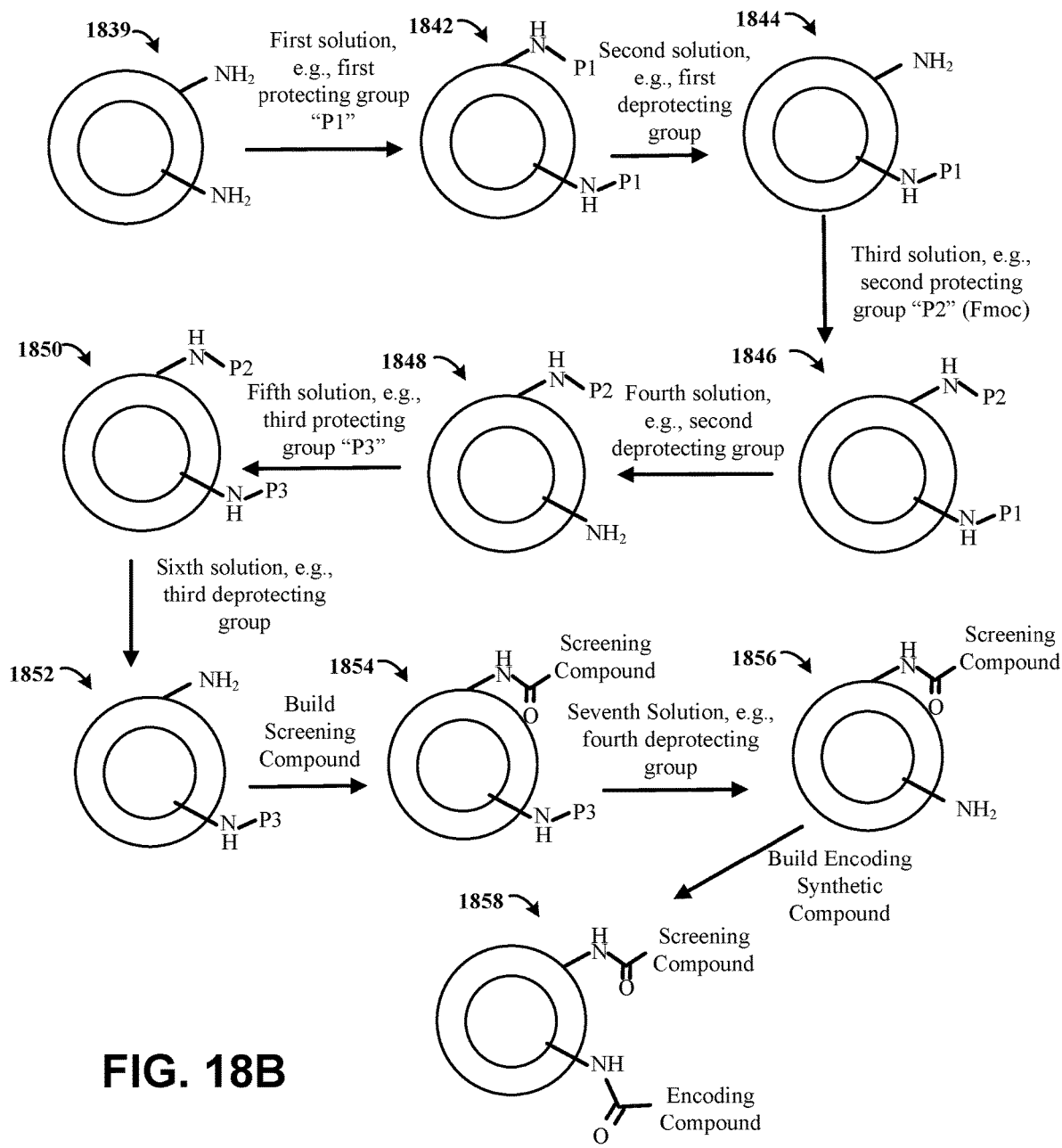

FIGS. 18A-18B illustrate an example process for topologically segregating a polymer bead, in accordance with various embodiments. FIG. 18A illustrates an example process for topologically segregating a polymer bead, in accordance with various embodiments. A topologically segregated polymer bead 1830 may be created using the process illustrated by FIG. 17, which can be further processed to generate a revised topologically segregated polymer bead 1838 having a screening compound in the exterior surface and an encoding compound in the interior surface using surface-functionalized groups (e.g., free amines). The topologically segregated polymer bead 1830 can be placed in contact with a first solution. The first solution can include another protecting group, such as an amine protecting group. For ease of reference, in the embodiment of FIG. 18A, the other protecting group is referred to as a "first protecting group", although in various embodiments the respective group is not the "first" protecting group in a sequence of reactions, as is illustrated by FIG. 18B. An example of the other protecting group can include fluorenylmethyloxycarbonyl chloride (Fmoc). Placing the topologically segregated polymer bead 1830 in contact with the first solution can cause a chemical reaction resulting in the polymer bead 1832 having an amine group double coupled to the first protecting group (e.g., Fmoc) in the exterior surface of the bead 1832.

The polymer bead 1832 is then caused to contact a second solution (sometimes referred to a third solution) that includes another deprotecting group. The other deprotecting group can be of a size that the group can penetrate the pores of the bead but does not deprotect the first protecting group (e.g., Fmoc) in the exterior surface. The second solution can include a thiophenol solution (e.g., thiophenol (PhSH)). Contacting the polymer bead 1832 with the second solution can result in deprotecting the protecting group in the interior surface, as illustrated by polymer bead 1834 which has a deprotected group (e.g., NH$_2$) in the interior surface, and a protected group coupled to the first protecting group in the exterior surface (e.g., NHFmoc). An additional deprotecting group, such as a tert-butyloxycarbonyl (Boc) group, is reacted with the polymer bead 1834 to couple the deprotected group (now a protected group) in the interior surface to Boc, as illustrated by the polymer bead 1836 having the protected group (e.g., another amine group) coupled to Boc in the interior surface. Example Boc groups include Boc-Ala and Boc-Ala-PAM. For ease of reference, in the embodiment of FIG. 18A, the additional protecting group is referred to as a "second protecting group", although in various embodiments the respective group is not the "second" protecting group in a sequence of reactions, as is illustrated by FIG. 18B.

In various embodiments, the first protecting group (e.g., Fmoc) in the exterior surface and the second protecting group (e.g., Boc) in the interior surface are used to cause the functional groups (e.g., the first and second amine groups) to be inert to various conditions. For example, the first functional group in the exterior surface is used to build a screening compound. The second functional group (e.g., the amine group) in the interior surface is used to build an encoding compound. The screening and encoding compounds are built using the functional amine groups via conventional chemical reactions and techniques, such as conventional coupling chemistry including peptide chemistry and solid-phase supported chemistry. Example techniques include assorted combinations of heat, pressure, and catalysis to alter chemical bonds, linear techniques, and repetitive bonding, among other techniques. For example, the functional groups can be reacted to form the polymer bead 1838 having a screening compound in the exterior surface and an encoding compound in the interior surface. The first and second protecting groups are used to control where the chemistry is performed by allowing for controlled and selective reactions of the functional groups. Fmoc groups can be removed using a base, such as piperidine, to expose the first amine group and Boc groups can be removed using an acid, such as TFA, to expose the second amine group. Depending on whether the encoded compound or the screening compound is to be built first, the location of the chemical coupling is controlled by either an acid or base deprotection that exposes the respective amine group and leaves the other amine group protected.

Such a process can be used to form a plurality of different beads. Each bead has a different screening compound and encoding compound attached thereto. In specific embodiments, the plurality of beads can form a library of screening compounds which can be used to screen and identify synthetic oligomers and polymers with new functions. An example screening process can include screening for compounds that selectively bind to a molecular target, such as a protein or nucleic acid. Another example includes screening for compounds that neutralize or kill a target, such as tumor cells, virus-infected cells and/or bacterial cells. The screening compounds in the library can be used for various functions including pharmaceutical drugs, reagents, sensors, catalysts, enzymes, or material used for particular purposes. The library can be screened to identify compounds (e.g., synthetic compounds) for different types of functions, which can include therapeutic, diagnostic, and/or industrial purposes. The compound, as selected and/or identified from the screening and mass spectrometry processes, and/or a conjugate form of the compound can be formed (using coupling chemistry) and used to provide a particular functionality.

The screening can include using a library of a plurality of different beads having different screening compounds in the bead exterior and different encoding compounds on the bead interior. An assay is performed with the beads to identify screening compounds on the exterior exhibiting a particular function. In a specific example, the assay can be used to bind to a protein, inhibit an enzyme, and neutralize or kill a cell, among other functions. The detected activity is assessed via a fluorescent readout of the assay using an optical scanner (e.g., to screen the assay for synthetic compounds that exhibit a function). Identified beads that are suspect of exhibiting the particular function or activity are identified based on the scan and removed from the screening plate and placed in wells or tubes. Removed beads are further processed to release the encoding compound on the bead interiors via chemical cleavage, as previously described. The encoding compounds are then read out using an analytical technique, such as mass spectrometry to identify the sequence of the plurality of molecules of the encoding compound and which maps to a respective screening compound. For example, as described above, the mass spectrometry characteristics of molecules forming the encoding compound are identified by performing mass spectrometry on a solution of the molecules cleaved from the polymer bead. The mass spectrometry characteristics of the molecules map to identification of the encoding compound sequence and which further maps to identification of the screening compound.

FIG. 18B an example process for topologically segregating a polymer bead, in accordance with various embodiments. The embodiment of FIG. 18B can illustrate a combination process as illustrated by FIG. 17 and FIG. 18A. A starting polymer bead 1839 is caused to contact a first solution containing a first protecting group, which is labelled "P1". The first protecting group can include DNs or Ns, as previously described. By contacting the bead 1839 with the first solution, the resulting bead 1842 is formed which includes a first protecting group (e.g., P1) in the interior and exterior surfaces.

The polymer bead 1842 is then caused to contact a second solution. The second solution can include a first deprotecting group, such as a protein having cysteines that selectively deprotect surface amines without deprotecting interior amines. The contact with the second solution results in the topologically segregated polymer bead 1844. The topologically segregated polymer bead 1844 includes a deprotected group in the exterior surface (e.g., $NH_2$) and a first protecting group (e.g., P1) in the interior surface.

The topologically segregated polymer bead 1844 is then placed in contact with a third solution. The third solution includes a second protecting group, such as an amine protecting group, which is labelled as "P2". An example of a second protecting group can include Fmoc. Placing the topologically segregated polymer bead 1844 in contact with the third solution can cause a chemical reaction resulting in the polymer bead 1846 having an amine group double coupled to the second protecting group (e.g., Fmoc) in the exterior surface of the bead 1846 and another amine group coupled to the first protecting group (e.g., DNs or Ns) in the interior surface.

The polymer bead 1846 is then caused to contact a fourth solution that includes second deprotecting group. The second deprotecting group can be of a size that the group can penetrate the pores of the bead but does not deprotect the second protecting group (e.g., Fmoc) in the exterior surface. The fourth solution can include a thiophenol solution (e.g., PhSH). Contacting the polymer bead 1846 with the fourth solution can result in deprotecting the second protecting group in the interior surface, as illustrated by polymer bead 1848 which has a deprotected group (e.g., $NH_2$) in the interior surface, and a protected group coupled to the second protecting group in the exterior surface (e.g., NHP2 or NHFmoc). The polymer bead 1848 is then placed in contact with a fifth solution that includes a third protecting group, which is labelled as "P3". The third protecting group, such as a Boc group, reacts with the polymer bead 1848 to couple the deprotected group (now a protected group) in the interior surface to the third protecting group. As illustrated by the polymer bead 1850, the resulting bead has the first protected group (e.g., an amine group) coupled to the second protecting group and a second protected group (e.g., another amine group) coupled to the third protecting group (e.g., Boc) in the interior surface. Example Boc groups include Boc-Ala and Boc-Ala-PAM.

As previously described, the second and third protecting groups (P2 and P3) are used to allow for controlled reaction of the respective amine groups. To control where coupling chemistry is performed, acid or base deprotection is performed. Specifically, one of the second and third protecting groups can deprotect with a base and the other with an acid. As an example, the second protecting group (P2) is Fmoc that is removed with a base, such as piperidine, and the third protecting group (P3) is Boc that is removed with an acid, such as TFA. Although embodiments are not so limited. As an example, the polymer bead 1850 is placed in contact with a sixth solution with includes a third deprotecting group. The third deprotecting group in this example removes the second protecting group (P2) to form the polymer bead 1852. The polymer bead 1852 has a free amine exposed in the exterior surface and a protected amine group in the interior surface. A screening compound is built using conventional couple chemistry to form the polymer bead 1854 having a screening compound in the exterior surface and the protected functional group is coupled to the third protecting group in the interior surface. The polymer bead 1854 is caused to contact a seventh solution that has a fourth deprotecting group used to deprotect the third protecting group (P3) in the interior, resulting in polymer bead 1856 having the screening compound in the exterior surface and a free amine group in the interior surface. An encoding compound is built using conventional couple chemistry to form the polymer bead 1858 having the screening compound in the exterior surface and an encoding compound in the interior surface. For example, as described above with respect to building the compound comprising the plurality of molecules with cleaving groups between, the encoding compound is built using mix-in-split coupling chemistry.

Although the embodiment of FIG. 18B illustrates the screening compound being built followed by the encoding compound, embodiments are not so limited. In various embodiments, the third protecting group is first removed and the encoding compound is built, followed by removal of the second protecting group and building of the screening compound. Further, various specific embodiments can include a polymer bead having an interior surface and an exterior surface topologically segregated from one another, where the interior surface includes an encoding compound and the exterior surface includes a protecting group (e.g., Fmoc). As may be appreciated, embodiments in accordance with the present disclosure are not limited to performance of each of the steps illustrated by FIG. 18B and can be directed to performance of different sub-steps illustrated. Further, various embodiments are directed to one or more of the different polymer beads illustrated by FIG. 18B (e.g., 1842, 1844, 1846, 1848, 1850, 1852, 1854, 1856, 1858). For example, the process can terminate at different steps of the process illustrated by FIG. 18B, resulting in different respective polymer beads.

Various embodiments include the surprising results of topologically segregated polymer beads. Specific embodiments include methods for spatial segregation of 10 micron Tentagel beads using reduced BSA for the deprotection of nitrobenzenesulfonamide groups present on the surface of the beads. The methods can be applied to the synthesis of polymer beads having Fmoc protecting group on the outside layer and Boc group on the inside.

Terms to exemplify orientation, such as in, on, exterior, interior, within, first, second, third, fourth, fifth, etc., may be used herein to refer to relative positions of elements as shown in the figures. It should be understood that the terminology is used for notational convenience only and that in actual use the disclosed structures may be oriented or ordered differently from the orientation or order shown in the figures. For example, a second deprotecting group may be used after a third deprotecting group. Thus, the terms should not be construed in a limiting manner.

Various embodiments are implemented in accordance with embodiments in U.S. Pat. Application (Ser. No. 15/498, 145), entitled "Topologically Segregated Polymer Beads and Methods Thereof", filed Apr. 26, 2017, which is fully incorporated herein by reference. For instance, the embodiments described therein may be combined in varying degrees (including wholly) with the embodiments described above. As a specific example, which is described above in connection with FIGS. 16-18B, a plurality of compounds that are each formed of molecules exhibiting distinguishable mass spectrometry characteristic, as described by various embodiments herein and illustrated at least by FIG. 1, can be implemented as the encoding compounds as described and illustrated by FIG. 2 of U.S. patent Ser. No. 15/498,145, which can be used to map to the respective screening compounds. Embodiments discussed in the US Pat. Application are not intended, in any way, to be limiting to the overall technical disclosure, or to any part of the claimed invention unless specifically noted.

Various embodiments described above, and discussed provisional application may be implemented together and/or in other manners. One or more of the items depicted in the present disclosure and in the underlying provisional application can also be implemented separately or in a more integrated manner, or removed and/or rendered as inoperable in certain cases, as is useful in accordance with particular applications. In view of the description herein, those skilled in the art will recognize that many changes may be made thereto without departing from the spirit and scope of the present disclosure.

What is claimed is:

1. A method comprising:
  using logic circuitry to:
    assign each of a plurality of subgroups to only one position in a sequence order for a plurality of prospective molecules, each of the plurality of subgroups exhibiting a mass spectrometry characteristic that is distinguishable from other subgroups in the plurality;
    select a plurality of molecules from the plurality of prospective molecules based on each including a unique sequence of a subset of m subgroups of the plurality of subgroups in the order of their assigned positions and each exhibiting a mass spectrometry characteristic that is distinguishable by a threshold value from mass spectrometry characteristics of other molecules of the plurality, wherein each of the plurality of subgroups are selected from a functional group and a monomer;
    assign each of the plurality of molecules to only one position in a sequence order of n number of positions for a plurality of synthetic compounds forming a library;
    define and store, as data in a memory circuit of the logic circuitry, each of the plurality of synthetic compounds as a unique sequence of a subset of n molecules of the plurality of molecules, one from each position in the sequence, and coupled together in the order of their assigned positions in the unique sequence and with cleavable groups positioned between each of the n molecules such that the n molecules are separatable from one another and the synthetic compounds are sequenceable via cleavage of the cleavable groups, mass spectrometry, and the distinguishable mass spectrometry characteristics of the n molecules;
    communicate the data defining the plurality of synthetic compounds to other circuitry; and
  using the other circuitry to receive the data defining the plurality of synthetic compounds and to form the plurality of synthetic compounds via coupling chemistry and based on the data defining the plurality of synthetic compounds, wherein the formed plurality of synthetic compounds are identifiable from one another via cleavage of the cleavable groups and the distinguishable mass spectrometry characteristics of the subset of n molecules as defined in the data, wherein the distinguishable mass spectrometry characteristics of the n molecules identify the n molecules, the order of the n molecules in each of the plurality of synthetic compounds, and the order of m subgroups forming each of the n molecules.

2. The method of claim 1, wherein the cleavable groups include poly-acrylamide (PAM) configured to cleave in response to contact with a solution containing NaOH or trifluoroacetic acid (TFA) such that each of the n molecules are separatable from one another. and selecting the plurality of molecules includes;
(1) using the logic circuitry to design molecules, and
(2) selecting the plurality of molecules that exhibit mass spectrometry characteristics separable from each other by the threshold value,
wherein each of the plurality of synthetic compounds includes the unique sequence of n molecules of the selected plurality of molecules that is sequenceable via mass spectrometry and which are each the unique sequence orders of n molecules from one another and the n molecules are each the unique sequence order of m subgroups of the plurality of subgroups, and each molecule of the selected plurality including the respective sequence of the subset of m subgroups of the plurality of subgroups as defined in the data,
wherein the mass spectrometry characteristic for each respective molecule as stored in the data identifies the respective position of the respective molecule in the sequence of the respective synthetic compound of the plurality and a composition of the respective molecule including the sequence of the subset of m subgroups of the plurality of subgroups which forms the respective molecule, and
wherein the mass spectrometry characteristics for each subgroup and each molecule include molecular weight, isotope distribution, elution time, or fragmentation pattern.

3. The method of claim 1, further including correlating the plurality of molecules with the assigned position in the sequence of the plurality of synthetic compounds, wherein each position in the sequence of the plurality of synthetic compounds includes a set of possible molecules among the plurality of molecules which is unique from sets of other positions in the sequence, and using the logic circuitry to define each of the plurality of synthetic compounds as different and unique sequential combination of the n molecules of the plurality of molecules based on the set of possible molecules for each of the n number of positions such that the mass spectrometry characteristic for each molecule of the plurality of molecules and as stored as data identifies the respective molecule, the position of the respective molecule in the respective synthetic compound, and the sequence of m sub-groups in the respective molecule.

4. The method of claim 1, wherein using the logic circuitry configured and arranged with the memory circuit to select the plurality of molecules includes:
selecting the plurality of subgroups that exhibit a mass spectrometry characteristic that is distinguishable by the threshold value from mass spectrometry characteristics of other subgroups in the plurality;
correlating, as data in the memory circuit, each of the plurality of subgroups with the assigned position in a sequence of prospective molecules used for forming the plurality of synthetic compounds based on the assignment; and
selecting the plurality of molecules among the prospective molecules that exhibit the mass spectrometry characteristics that are distinguishable by the threshold value from other mass spectrometry characteristics.

5. The method of claim 4, wherein correlating each of the plurality of subgroups to the position in the sequence includes selecting, using the logic circuitry, a set of subgroups among the plurality of subgroups for each m position in the molecules.

6. The method of claim 1, wherein the data defines the plurality of molecules with the assigned positions in the unique sequence of n molecules of the plurality of synthetic compounds and the plurality of subgroups with the assigned positions in the unique sequence of m subgroups of the n molecules.

7. The method of claim 1, further including performing mass spectrometry on the plurality of molecules to generate a reference pattern used for error control and storing the reference pattern via the memory circuit, wherein the mass spectrometry characteristic includes a property selected from the group consisting of: molecular weight, fragmentation pattern, isotope distribution, and a combination thereof.

8. The method of claim 1, further including screening the plurality of synthetic compounds for a particular physical function and selecting a synthetic compound among the plurality of synthetic compounds that exhibits the particular function.

9. The method of claim 1, wherein using the logic circuitry to assign each of the plurality of molecules to the position in the unique sequence order of n positions includes correlating, as data in the memory circuit, the assigned positions of the selected plurality of molecules in the sequence order of n number of positions with the respective mass spectrometry characteristics and the unique sequence order of m subgroups of the plurality of subgroups of each of the selected plurality of molecules, wherein each position in the sequence order of the n number of positions includes a set of possible molecules among the plurality of molecules.

10. The method of claim 9, wherein using the logic circuitry to define each of the plurality of synthetic compounds as the unique sequence of n molecules includes selecting unique sequence orders of the n molecules based on the set of possible molecules for each of the n number of positions and defining the plurality of synthetic compounds as different sequential combination of the n molecules in the data based on the selection and as associated with the correlation of the n molecules with the assigned positions and mass spectrometry characteristics, and each molecule is assigned to only one of the n number of positions of the sequence order.

11. The method of claim 1, wherein the cleavable groups are configured to cleave in response to contact with a solution containing NaOH or trifluoroacetic acid (TFA) such that each of the n molecules of each of the plurality of synthetic compounds are separatable from one another the distinguishable mass spectrometry characteristic for each of the plurality of molecules identifies:
the respective molecule among the plurality of molecules including the position of the respective molecule within the respective synthetic compound among the plurality of synthetic compounds, and the unique sequence of m subgroups forming the respective molecule.

12. The method of claim 1, wherein the distinguishable mass spectrometry characteristic for each of the selected plurality of molecules includes a molecular weight which is distinguishable from molecular weights of the other molecules of the plurality, wherein at least a portion of the plurality of subgroups include amino acids.

* * * * *